(«12») United States Patent
Arntzen et al.

(10) Patent No.: US 7,094,606 B2
(45) Date of Patent: Aug. 22, 2006

(54) USE OF MIXED DUPLEX OLIGONUCLEOTIDES TO EFFECT LOCALIZED GENETIC CHANGES IN PLANTS

(76) Inventors: Charles J. Arntzen, 1005 Highland Rd., Ithaca, NY (US) 14850; Peter B. Kipp, 700 Warren Rd., Apt. 11-3E, Ithaca, NY (US) 14850; Ramesh Kumar, 60 Yard Rd., Pennington, NJ (US) 08534; Gregory D. May, 303 The Parkway, Ithaca, NY (US) 14850

( * ) Notice: Subject to any disclaimer, the term of this patent is extended or adjusted under 35 U.S.C. 154(b) by 130 days.

(21) Appl. No.: 09/129,298

(22) Filed: Aug. 5, 1998

(65) Prior Publication Data

US 2003/0196218 A1 Oct. 16, 2003

Related U.S. Application Data

(60) Provisional application No. 60/054,836, filed on Aug. 5, 1997.

(51) Int. Cl.
*C12N 15/82* (2006.01)
(52) U.S. Cl. ...................................... 435/470; 800/300
(58) Field of Classification Search ................ 800/278, 800/290, 300, 306, 317.3, 320, 322; 435/459, 435/6, 463, 285.3
See application file for complete search history.

(56) References Cited

U.S. PATENT DOCUMENTS

| | | | |
|---|---|---|---|
| 4,945,050 A | | 7/1990 | Sanford et al. |
| 5,013,659 A | | 5/1991 | Bedbrook et al. |
| 5,100,792 A | | 3/1992 | Sanford et al. |
| 5,204,253 A | * | 4/1993 | Sanford et al. ............. 435/459 |
| 5,302,523 A | | 4/1994 | Coffee et al. |
| 5,378,824 A | | 1/1995 | Bedbrook et al. |
| 5,384,253 A | | 1/1995 | Krzyzek et al. |
| 5,565,350 A | * | 10/1996 | Kmiec ............................ 435/6 |
| 5,684,232 A | * | 11/1997 | Horn et al. .................. 800/298 |
| 5,731,181 A | * | 3/1998 | Kmiec ............................ 435/6 |
| 5,760,012 A | | 6/1998 | Kmiec et al. |
| 5,948,954 A | * | 9/1999 | Horn et al. .................. 800/264 |
| 5,965,755 A | * | 10/1999 | Sernyk et al. ................. 554/5 |

FOREIGN PATENT DOCUMENTS

| | | |
|---|---|---|
| WO | WO 95/15972 A1 | 6/1995 |
| WO | WO 97/48714 A1 | 12/1997 |
| WO | WO 98/54330 A1 | 12/1998 |
| WO | WO 99/25853 A1 | 5/1999 |
| WO | WO 99/58702 A1 | 11/1999 |

OTHER PUBLICATIONS

Dunder et al 1995, Maize transformation by microprojectile bombardment of immature embryos, in Gene Transfer To Plants, Potrykus and Spangenberg, Eds., Springer Verlag publisher. Chapter 15, pp. 127-138.*
Hohn and Puchta, Jul. 1999, Gene therapy in plants. Proceedings of the National Academy of Science, USA 96:8321-8323.*
Svab et al 1990, Stable transformation of plastids in higher plants. Proc. Natl. Acad. Sci. USA 87:8526-8530.*
Gene Transfer To Plants, 1995, Potrykus and Spangenberg, Eds., Chapers 14-20, Springer Lab Manual, Springer Verlag, pp. 115-169.*
Sanford et al 1993, Optimizing the biolistic process for different biological applications. Methods in Enzymology 217:483-509.*
Wang et al 2000, Identification of a novel plant virus promoter using a potyvirus infectious clone. Virus Genes 20(1):11-17.*
Tsugane et al 1999, A recessive Arabidopsis mutant that grows photoautotrophically under salt stress shows enhanced active oxygen detoxification. The Plant Cell 11:1195-1206.*
Cole-Strauss, A., et al., "Correction of the Mutation Responsible for Sickle Cell Anemia by an RNA-DNA Oligonucleotide", Science, vol. 273, pp. 1386-1389, Sep. 6, 1996.
Svab, Z., et al., "Stable Transformation of Plastids in Higher Plants", 1990, Proceedings of the National Academy of the Sciences USA, vol. 87, 8526, 8530.
Svab, Z. et al., "High Frequency Plastid Transformation in Tobacco by Selection for a Chimeric aadA Gene", 1993, Proceedings of the National Academy of the Sciences USA, vol. 90, 913-917.
Yoon, K., et al., "Targeted gene correction of episomal DNA in mammalian cells mediated by a chimeric RNA-DNA oligonucleotide", Proceedings of the National Academy of the Sciences USA, vol. 93, pp. 2071-2076, Mar. 1996.
Beetham, P. R., Kipp, P. B., Sawycky, X. L., Arntzen, C. J., May, G. D. (Jul. 1999) "A tool for functional plant genomics: Chimeric RNA/DNA oligonucleotides cause *in vivo* gene-specific mutations" *Proc. Natl. Acad. Sci. USA*96:8774-8778.
Cole-Strauss, A., Yoon, K., Xiang, Y., Byrne, B. C., Rice, M. C., Gryn, J., Holloman, W. K., Kmiec, E. B. (Sep. 1996) "Correction of the Mutation Responsible for Sickle Cell Anemia by an RNA-DNA Oligonucleotide" *Science*273: 1386-1389.
Holmes, Jr. J., Clark, S., Modric, P. (Aug. 1990) "Strand-specific mismatch correction in nuclear extracts of human and *Drosophila melanogaster* cell lines" *Proc. Natl. Acad. Sci. USa* 87:5837-5841.
Kmiec, E. B. (Jun. 1995) "Genetic manipulation in mammalian cells using an RNA/DNA chimeric oligonucleotide" *Advanced Drug Delivery Reviews*.
Zhu, T., Peterson, D. J., Tagliani, L., St. Clair, G., Baszczynski, C. L., Bowen, B. (Jul. 1999) "Targeted manipulation of maize genes *in vivo* using chimeric RNA/DNA oligonucleotides" *Proc. Natl. Acad. Sci. USA*96:8768-8773.

* cited by examiner

*Primary Examiner*—David H Kruse
(74) *Attorney, Agent, or Firm*—Saliwanchik, Lloyd & Saliwanchik

(57) ABSTRACT

The invention concerns the use of duplex oligonucleotides about 25 to 30 base pairs to introduce site specific genetic alterations in plant cells. The oligonucleotides can be delivered by mechanical (biolistic) systems or by electrpoporation of plant protoplasts. Thereafter plants having the genetic alteration can be generated from the altered cells. In specific embodiments the invention concerns alteration in the gene that encode acid invertase, UDP-glucose pyrophosphorylase, polyphenol oxidase, O-methyl transferase, cinnamyl alcohol dehydrogenase, ACC synthase and ACC oxidase or etr-1 or a homolog of etr-1, and plants having isolated point mutations in such genes.

16 Claims, No Drawings

US 7,094,606 B2

USE OF MIXED DUPLEX OLIGONUCLEOTIDES TO EFFECT LOCALIZED GENETIC CHANGES IN PLANTS

CROSS-REFERENCE TO A RELATED APPLICATION

This application claims the benefit of U.S. Provisional Application Ser. No. 60/054,836, filed Aug. 5, 1997.

1. FIELD OF THE INVENTION

The field of the present invention relates to methods for the improvement of existing lines of plants and to the development of new lines having desired traits. The previously available methods of obtaining genetically altered plants by recombinant DNA technology enabled the introduction of preconstructed exogenous genes in random, atopic positions, so-called transgenes. In contrast the present invention allows the skilled practitioner to make a specific alteration of a specific pre-existing gene of a plant. The invention utilizes duplex oligonucleotides having a mixture of RNA-like nucleotides and DNA-like nucleotides to effect the alterations, hereafter "mixed duplex oligonucleotides" or MDON.

2. BACKGROUND TO THE INVENTION

2.1 MDON and their Use to Effect Specific Genetic Alterations

Mixed duplex oligonucleotides (MDON) and their use to effect genetic changes in eukaryotic cells are described in U.S. Pat. No. 5,565,350 to Kmiec (Kmiec I). Kmiec I discloses inter alia MDON having two strands, in which a first strand contains two segments of at least 8 RNA-like nucleotides that are separated by a third segment of from 4 to about 50 DNA-like nucleotides, termed an "interposed DNA segment." The nucleotides of the first strand are base paired to DNA-like nucleotides of a second strand. The first and second strands are additionally linked by a segment of single stranded nucleotides so that the first and second strands are parts of a single oligonucleotide chain. Kmiec I further teaches a method for introducing specific genetic alterations into a target gene. According to Kmiec I, the sequences of the RNA segments are selected to be homologous, i.e., identical, to the sequence of a first and a second fragment of the target gene. The sequence of the interposed DNA segment is homologous with the sequence of the target gene between the first and second fragment except for a region of difference, termed the "heterologous region." The heterologous region can effect an insertion or deletion, or can contain one or more bases that are mismatched with the sequence of target gene so as to effect a substitution. According to Kmiec I, the sequence of the target gene is altered as directed by the heterologous region, such that the target gene becomes homologous with the sequence of the MDON. Kmiec I specifically teaches that ribose and 2'-Om-ethylribose, i.e., 2'-methoxyribose, containing nucleotides can be used in MDON and that naturally-occurring deoxyribose-containing nucleotides can be used as DNA-like nucleotides.

U.S. patent application Ser. No. 08\664,487, filed Jun. 17, 1996, now U.S. Pat. No. 5,731,181 (Kmiec II) does specifically disclose the use of MDON to effect genetic changes in plant cells and discloses further examples of analogs and derivatives of RNA-like and DNA-like nucleotides that can be used to effect genetic changes in specific target genes.

Scientific publications disclosing uses of MDON having interposed DNA segments include Yoon, et al., 1996, *Proc. Natl. Acad. Sci.* 93:2071–2076 and Cole-Straus, A. et al., 1996, *SCIENCE* 273:1386–1389. The scientific publications disclose that rates of mutation as high as about one cell in ten can be obtained using liposomal mediated delivery. However, the scientific publications do not disclose that MDON can be used to make genetic changes in plant cells.

The present specification uses the term MDON, which should be understood to be synonymous with the terms "chimeric mutation vector," "chimeric repair vector" and "chimeraplast" which are used elsewhere.

2.2 Transgenic Plant Cells and the Generation of Plants from Transgenic Plant Cells Of the techniques taught by Kmiec I and II for delivery of MDON into the target cell, the technique that is most applicable for use with plant cells is the electroporation of protoplasts. The regeneration of fertile plants from protoplast cultures has been reported for certain species of dicotyledonous plants, e.g., *Nicotiana tobacum* (tobacco), U.S. Pat. No. 5,231,019 and Fromm, M. E., et al., 1988, Nature 312, 791, and soybean variety *Glycine max*, WO 92/17598 to Widholm, J. M. However, despite the reports of isolated successes using non-transformed cells, Prioli, L. M., et al., Bio/technology 7, 589, Shillito, R. D., et al., 1989, Bio/Technology 7, 581, the regeneration of fertile monocotyledonous plants from transformed protoplast cultures is not regarded as obtainable with application of routine skill. Frequently, transformed protoplasts of monocotyledonous plants result in non-regenerable tissue or, if the tissue is regenerated the resultant plant is not fertile.

Other techniques to obtain transformed plant cells by introducing kilobase-sized plasmid DNA into plant cells having intact or partially intact cell walls have been developed. U.S. Pat. No. 4,945,050, U.S. Pat. No. 5,100,792 and U.S. Pat. No. 5,204,253 concern the delivery of plasmids into intact plant cells by adhering the plasmid to a microparticle that is ballistically propelled across the cell wall, hereafter "biolistically transformed" cell. For example U.S. Pat. No. 5,489,520 describes the regeneration of a fertile *maize* plant from a biolistically transformed cell. Other techniques for the introduction of plasmid DNA into suspensions of plant cells having intact cell walls include the use of silicon carbide fibers to pierce the cell wall, see U.S. Pat. No. 5,302,523 to Coffee R., and Dunwell, J. M.

A technique that allows for the electroporation of *maize* cells having a complex cell wall is reported in U.S. Pat. No. 5,384,253 to Krzyzek, Laursen and P. C. Anderson. The technique uses a combination of the enzymes endopectin lyase (E.C. 3.2.1.15) and endopolygalacturonase (E.C. 4.2.2.3) to generate transformation competent cells that can be more readily regenerated into fertile plants than true protoplasts. However, the technique is reported to be useful only for F1 cell lines from the cross of line A188×line B73.

3. SUMMARY OF THE INVENTION

The present invention provides new methods of use of the MDON that are particularly suitable for use in such plant cells.

Thus one aspect of the invention is techniques to adhere MDON to particles which can be projected through the cell wall to release the MDON within the cell in order to cause a mutation in a target gene of the plant cell. The mutations that can be introduced by this technique are mutations that confer a growth advantage to the mutated cells under appropriate conditions and mutations that cause a phenotype that can be detected by visual inspection. Such mutations are termed "selectable mutations."

In a further embodiment the invention encompasses a method of introducing a mutation other than a selectable mutation into a target gene of a plant cell by a process which includes the steps of introducing a mixture of a first MDON that introduces a selectable mutation in the plant cell and a second MDON that causes the non-selectable mutation.

The invention further encompasses the culture of the cells mutated according to the foregoing embodiments of the invention so as to obtain a plant that produces seeds, henceforth a "fertile plant," and the production of seeds and additional plants from such a fertile plant.

The invention further encompasses fertile plants having novel characteristics which can be produced by the methods of the invention.

4. DETAILED DESCRIPTION OF THE INVENTION

4.1 Recombinagenic Oligonucleobases and Mixed Duplex OligoNucleotides

The invention can be practiced with MDON having the conformations and chemistries described in Kmiec I or in Kmiec II, which are hereby incorporated by reference. The MDON of Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Commonly assigned U.S. patent application Ser. No. 09/078,063, filed May 12, 1998, and Ser. No. 09/078,064, filed May 12, 1998, which are each hereby incorporated in their entirety, disclose additional molecules that can be used for the present invention. The term "recombinagenic oligonucleobase" is used herein to denote the molecules that can be used in the present invention. Recombinagenic oligonucleobases include MDON, non-nucleotide containing molecules taught in Kmiec II and the molecules taught in the above noted commonly assigned patent applications.

In a preferred embodiment the RNA-type nucleotides of the MDON are made Rnase resistant by having replacing the 2'-hydroxyl with a fluoro, chloro or bromo functionality or by placing a substituent on the 2'-O. Suitable substituents include the substituents taught by the Kmiec II, $C_{1-6}$ alkane. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a MDON by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

A particular embodiment of the invention comprises MDON that are linked solely by unsubstituted phosphodiester bonds. Alternatively embodiments comprise linkage by substituted phosphodiesters, phosphodiester derivatives and non-phosphorus-based linkages as taught by Kmiec II. A further particular embodiment comprises MDON wherein each RNA-type nucleotide is a 2'-Substituted Nucleotide. Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. In more preferred embodiments of 2'-Substituted Ribonucleotides are 2'-fluoro, 2'-methoxy, 2'-methoxyethyloxy, and 2'-allyloxy substituted nucleotides. In one embodiment the MDON oligomer is linked by unsubstituted phosphodiester bonds.

Although MDON having only a single type of 2'-substituted RNA-type nucleotide are more conveniently synthesized, the invention can be practiced with MDON having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The MDON of the invention preferably have fewer than 100 nucleotides and more preferably fewer than 85 nucleotides, but more than 50 nucleotides. The first and second strands are Watson-Crick base paired. In one embodiment the strands of the MDON are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the MDON may differ from the sequence of the target gene only by the deletion of one, two, three, or five or fewer nucleotides from the MDON. The length and position of the heterologous region is, in this case, deemed to be the length of the deletion, even though no nucleotides of the MDON are within the heterologous region. The distance between the fragments of the target gene that are complementary to the two homologous regions is identically the length of the heterologous region when a substitution or substitutions is intended. When the heterologous region contains an insertion, the homologous regions are thereby separated in the MDON farther than their complementary homologous fragments are in the gene, and the converse is applicable when the heterologous region encodes a deletion.

The RNA segments of the MDON are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18–22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a MDON is termed a "mutator segment."

Commonly assigned U.S. patent application Ser. No. 09/078,063, filed May 12, 1998, and Ser. No. 09/078,064, filed May 12, 1998, disclose a type of duplex recombinagenic oligonucleobase in which a strand has a sequence that is identical to that of the target gene and only the sequence of the "complementary" strand contains a heterologous region. This configuration results in one or more mismatched bases or a "heteroduplex" structure. The heterologous region of the heteroduplex recombinagenic oligonucleobases that are useful in the present invention is located in the strand that contains the deoxynucleotides. In one embodiment, the heterologous region is located on the strand that contains the 5' terminal nucleotide.

4.2 The Location and Type of Mutation Introduced by a MDON

Frequently, the design of the MDON for use in plant cells must be modified from the designs taught in Kmiec I and II. In mammalian and yeast cells, the genetic alteration introduced by a MDON that differs from the target gene at one position is the replacement of the nucleotide in the target gene at the mismatched position by a nucleotide complementary to the nucleotide of the MDON at the mismatched position. By contrast, in plant cells there can be an alteration of the nucleotide one base 5' to the mismatched position on the strand that is complementary to the strand that contains the DNA mutator segment. The nucleotide of the target gene is replaced by a nucleotide complementary to the nucleotide of the DNA mutator segment at the mismatched position. Consequently, the mutated target gene differs from the MDON at two positions.

The mutations introduced into the target gene by a MDON are located between the regions of the target gene that are homologous with the ribonucleotide portion of the homology regions of the MDON, henceforth the "RNA segments." The specific mutation that is introduced depends upon the sequence of the heterologous region. An insertion or deletion in the target gene can be introduced by using a heterologous region that contains an insertion or deletion, respectively. A substitution in the target gene can be obtained by using a MDON having a mismatch in the heterologous region of the MDON. In the most frequent embodiments, the mismatch will convert the existing base of the target gene into the base that is complementary to the mismatched base of the MDON. The location of the substitution in the target gene can be either at the position that corresponds to the mismatch or, more frequently, the substitution will be located at the position on the target strand immediately 5' to the position of the mismatch, i.e., complementary to the position of the MDON immediately 3' of the mismatched base of the MDON.

The relative frequency of each location of the mismatch-caused substitution will be characteristic of a given gene and cell type. Thus, those skilled in the art will appreciate that a preliminary study to determine the location of substitutions in the gene of particular interest is generally indicated, when the location of the substitution is critical to the practice of the invention.

4.3 The Delivery of MDON by Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. No. 4,945,050, U.S. Pat. No. 5,100,792 and U.S. Pat. No. 5,204,253 concern general techniques for selecting microcarriers and devices for projecting them.

The conditions that are used to adhere DNA fragments to the microcarriers are not suitable for the use of MDON. The invention provides techniques for adhering sufficient amounts of MDON to the microcarrier so that biolistic delivery can be employed. In a suitable technique, ice cold microcarriers (60 mg/ml), MDON (60 mg/ml) 2.5 M $CaCl_2$ and 0.1 M spermidine are added in that order; the mixture gently agitated, e.g., by vortexing, for 10 min and allowed to stand at room temperature for 10 min whereupon the microcarriers are diluted in 5 volumes of ethanol, centrifuged and resuspended in 100% ethanol. Good results can be obtained with a concentration in the adhering solution of 8–10 μg/μl microcarriers, 14–17 μg/ml MDON, 1.1–1.4 M $CaCl_2$ and 18–22 mM spermidine. Optimal results were observed under the conditions of 8 μg/μl microcarriers, 16.5 μg/ml MDON, 1.3 M $CaCl_2$ and 21 mM spermidine.

MDON can also be introduced into plant cells for the practice of the invention using microfibers to penetrate the cell wall and cell membrane. U.S. Pat. No. 5,302,523 to Coffee et al. describes the use of 30×0.5 μm and 10×0.3 μm silicon carbide fibers to facilitate transformation of suspension *maize* cultures of Black Mexican Sweet. Any mechanical technique that can be used to introduce DNA for transformation of a plant cell using microfibers can be used to deliver MDON for transmutation.

A suitable technique for microfiber delivery of MDON is as follows. Sterile microfibers (2 μg) are suspended in 150 μl of plant culture medium containing about 10 μg of MDON. A suspension culture is allowed to settle and equal volumes of packed cells and the sterile fiber/MDON suspension are vortexed for 10 minutes and plated. Selective media are applied immediately or with a delay of up to about 120 hours as is appropriate for the particular trait.

The techniques that can be used to deliver MDON to transmute nuclear genes can also be used to cause transmutation of the genes of a plastid of a plant cell. Plastid transformation of higher plants by biolistic delivery of a plasmid followed by an illegitimate recombinatorial insertion of the plasmid is well known to those skilled in the art. Svab, Z., et al., 1990, Proc. Natl. Acad. Sci. 87, 8526–8530. The initial experiments showed rates of transformation that were between 10-fold and 100-fold less than the rate of nuclear transformation. Subsequent experiments showed that rates of plasmid transformation comparable to the rate of nuclear transformation could be achieved by use of a dominant selectable trait such as a bacterial aminoglycoside 3'-adenosyltransferase gene, which confers spectinomycin resistance. Svab, Z., & Maliga, P., 1993, Proc. Natl. Acad. Sci. 90, 913–917.

According to the invention MDON for the transmutation of plastid genes can be introduced into plastids by the same techniques as above. When the mutation desired to be introduced is a selectable mutation the MDON can be used alone. When the desired mutation is non-selectable the relevant MDON can be introduced along with a MDON that introduces a selectable plastid mutation, e.g., a mutation in the psbA gene that confers triazine resistance, or in combination with a linear or circular plasmid that confers a selectable trait.

The foregoing techniques can be adapted for use with recombinagenic oligonucleobases other than MDON.

4.4 Protoplast Electroporation

In an alternative embodiment the recombinagenic oligonucleobase can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al., 1996, in Methods in Molecular Biology 55, 89–107 (Humana Press, Totowa, N.J.). The protoplasts need not be cultured in growth media prior to electroporation.

Suitable conditions for electroporation are $3 \times 10^5$ protoplasts in a total volume of 0.3 ml with a concentration of MDON of between 0.6–4 µg/mL.

4.5 The Introduction of Mutations

The invention can be used to effect genetic changes, herein "transmutate," in plant cells. In an embodiment the plant cells have cell walls, i.e., are other than protoplasts.

The use of MDON to transmutate plant cells can be facilitated by co-introducing a trait that allows for the ready differentiation and separation of cells (hereafter "selection") into which MDON have been introduced from those that have not. In one embodiment of the invention the selection is performed by forming a mixture of MDON and a plasmid that causes the transient expression of a gene that confers a selectable trait, i.e., one that permits survival under certain conditions, e.g., a kanamycin resistance gene. Under these circumstances elimination of cells lacking the selectable trait removes the cells into which MDON were not introduced. The use of a transient expression plasmid to introduce the selectable trait allows for the successive introduction of multiple genetic changes into a plant cell by repeatedly using a single standardized selection protocol.

In an alternative embodiment transmutation can be used to introduce a selectable trait. A mixture of a first MDON that causes a selectable mutation in a first target gene and a second MDON that causes a non-selectable mutation in a second target gene is prepared. According to the invention, at least about 1% of the cells having the selectable mutation will be found to also contain a mutation in the second target gene that was introduced by the second MDON. More frequently at least about 10% of the cells having the selectable mutation will be found to also contain a mutation in the second target gene.

One use of this embodiment of the invention is the investigation of the function of a gene-of-interest. A mixture is provided of a MDON that causes a selectable mutation and a MDON that causes a mutation that would be expected to "knock-out" the gene-of-interest, e.g., the insertion of a stop codon or a frameshift mutation. Cells in which one or more copies of the gene-of-interest have been knocked out can be recovered from the population having the selectable mutation. Such cells can be regenerated into a plant so that the function of the gene-of-interest can be determined.

A selectable trait can be caused by any mutation that causes a phenotypic change that can produce a selective growth advantage under the appropriate selective conditions or a phenotypic change that can be readily observed, such as change in color of the plant cells growing in a callus. The selectable trait can itself be a desirable traits, e.g., herbicide resistance, or the selectable trait can be used merely to facilitate the isolation of plants having a non-selectable trait that was introduced by transmutation. A desired nonselectable trait can be introduced into a cell by using a mixture of the MDON that causes the desired mutation and the MDON that causes the selectable mutation, followed by culture under the selecting conditions. Selection according to this scheme has the advantage of ensuring that each selected cell not only received the mixture of MDONs, but also that the cell which received the mixture was then susceptible to transmutation by a MDON.

A mutation that causes a lethal phenotypic change under the appropriate conditions, termed a negatively selectable mutation, can also be used in the present invention. Such mutations cause negatively selectable traits. Negatively selectable traits can be selected by making replica plates of the transmutated cells, selecting one of the replicas and recovering the transmutated cell having the desired property from the non-selected replica.

4.6 Specific Genes That Can Be Transmutated to Create Selectable Traits

In one embodiment of the invention a MDON is used to introduce a mutation into an Acetolactate synthase (ALS) gene, which is also termed the aceto-hydroxy amino acid synthase (AHAS) gene. Sulfonylurea herbicides and imidazoline herbicides are inhibitors of the wild type ALS enzymes. Dominant mutations that render plants resistant to the actions of sulfonylureas and imidazolines have been described. See U.S. Pat. Nos. 5,013,659 and 5,378,824 (Bedbrook) and Rajasekaran K., et al., 1996, Mol. Breeding 2, 307–319 (Rajasekaran). Bedbrook at Table 2 describes several mutations (hereafter, a "Bedbrook Mutation") that were found to render yeast ALS enzymes resistant to sulfonylurea herbicides. Bedbrook states that each of the Bedbrook mutations makes a plant resistant to sulfonylurea and imidazoline herbicides when introduced into a plant ALS gene. It is understood that in most plants the gene encoding ALS has been duplicated. A mutation can be introduced into any allele of either ALS gene.

Three of the Bedbrook mutations were, in fact, shown to confer herbicide resistance in a plant, namely the substitutions Pro→Ala$^{197}$, Ala→Asp$^{205}$ and Trp→Leu$^{591}$. Rajasekaran reports that mutations Trp→Ser$^{591}$ caused resistance to sulfonylurea and imidazoline and that Ser→Asn$^{660}$ caused resistance to imidazoline herbicides. The results of Rajasekaran are reported herein using the sequence numbering of Bedbrook. Those skilled in the art will understand that the ALS genes of different plants are of unequal lengths. For clarity, a numbering system is used in which homologous positions are designated by the same position number in each species. Thus, the designated position of a mutation is determined by the sequence that surrounds it. For example, the mutation Trp→Ser$^{591}$ of Rajasekaran is at residue 563 of the cotton ALS gene but is designated as position 591 of Bedbrook because the mutated Trp is surrounded by the sequence that surrounds Trp$^{591}$ in Table 2 of Bedbrook. According to the invention any substitution for the naturally occurring amino and at position 660 or one of the positions listed in Table 2 of Bedbrook, which is hereby incorporated by reference, can be used to make a selectable mutation in the ALS gene of a plant.

In a further embodiment of the invention the selectable mutation can be a mutation in the chloroplast gene psbA that encodes the D1 subunit of photosystem II, see Hirschberg, J., et al., 1984, Z. Naturforsch. 39, 412–420 and Ohad, N., & Hirschberg, J., The Plant Cell 4, 273–282. Hirschberg et al. reports that the mutation Ser→Gly$^{264}$ results in resistance to triazine herbicides, e.g.,2-Cl-4-ethylamino-6-isopropylamino-s-triazine (Atrazine). Other mutations in the psbA gene that cause Atrazine herbicide resistance are described in Erickson J. M., et al., 1989, Plant Cell 1, 361–371, (hereafter an "Erickson mutation"), which is hereby incorporated by reference. The use of the selectable trait caused by an Erickson mutation is preferred when it is desired to introduce a second new trait into a chloroplast.

The scientific literature contains further reports of other mutations that produce selectable traits. Ghislain M., et al., 1995, The Plant Journal 8, 733–743, describes a Asn→Ile$^{104}$ mutation in the *Nicotiana sylvestris* dihydrodipicolinate synthase (DHDPS, EC 4.2.1.52) gene that results in resistance to S-(2-aminoethyl)L-cysteine. Mourad, G., & King, J., 1995, Plant Physiology 109, 43–52 describes a mutation in the threonine dehydratase of *Arabidopsis thaliana* that results in resistance to L-O-methylthreonine. Nelson, J. A. E., et al., 1994, Mol. Cell. Biol. 14, 4011–4019 describes the substitution of the C-terminal Leu of the S14/rp59 ribosomal protein by Pro, which causes resistance to the translational inhibitors crytopluerine and emetine. In further embodiments of the invention, each of the foregoing mutations can be used to create a selectable trait. Each of Ghislain, Mourad and Nelson are hereby incorporated by reference.

4.7 Genes that can be Mutated to Create Desirable Non-Selectable Traits

EXAMPLE 1

Male Sterility

Certain commercially grown plants are routinely grown from hybrid seed including corn (*maize, Zea maize*), tomatoes and most other vegetables. The production of hybrid seed requires that plants of one purebred line be pollinated only by pollen from another purebred line, i.e., that there be no self pollination. The removal of the pollen-producing organs from the purebred parental plants is a laborious and expensive process. Therefore, a mutation that induces male-sterility i.e., suppresses pollen production or function, would obviate the need for such process.

Several genes have been identified that are necessary for the maturation or function of pollen but are not essential for other processes of the plant. Chalcone synthase (chs) is the key enzyme in the synthesis of flavonoids, which are pigments found in flowers and pollen. Inhibition of chs by the introduction of a chs antisense expressing gene in the petunia results in male sterility of the plant. Van der Meer, I. M., et al., 1992, The Plant Cell 4, 253–262. There is a family of chs genes in most plants. See, e.g., Koes, R. E., et al., 1989, Plant Mol. Biol. 12, 213–226. Likewise disruption of the chalcone synthase gene in *maize* by insertion of a transposable element results in male sterility. Coe, E. H., J. Hered. 72, 318–320. The structure of *maize* chalcone synthase and a duplicate gene, whp, is given in Franken, P., et al., 1991, EMBO J. 10, 2605–2612. Typically in plants each member of a multigene family is expressed only in a limited range of tissues. Accordingly, the present embodiment of the invention requires that in species having multiple copies of chalcone synthase genes, the particular chs gene or genes expressed in the anthers be identified and interrupted by introduction of a frameshift, and one or more in-frame termination codons or by interruption of the promoter.

A second gene that has been identified as essential for the production of pollen is termed Lat52 in tomato. Muschietti, J., et al., 1994, The Plant Journal 6, 321–338. LAT52 is a secreted glycoprotein that is related to a trypsin inhibitor. Homologs of Lat52 have been identified in *maize* (termed Zm13, Hanson D. D., et al., 1989 Plant Cell 1, 173–179; Twell D., et al., 1989, Mol. Gen. Genet. 217, 240–245), rice (termed Ps1, Zou J., et al., 1994 Am. J. Bot. 81, 552–561 and olive (termed Ole e I, Villalba, M., et al., 1993, Eur. J. Biochem. 276, 863–869). Accordingly, the present embodiment of the invention provides for a method of obtaining male sterility by the interruption of the Lat52/Zm13 gene or its homologs by the introduction of a frameshift, one or more in-frame termination codons or by interruption of the promoter.

A third gene that has been identified as essential for the production of pollen is the gene that encodes phenylalanine ammonium lyase (PAL, EC 4.3.1.5). PAL is an essential enzyme in the production of both phenylpropanoids and flavonoids. Because phenylpropanoids are a precursor to lignins, which can be an essential for the resistance to disease in the preferred embodiment a PAL isozyme that is expressed only in the anther is identified and interrupted to obtain male sterility.

EXAMPLE 2

Alteration of Carbohydrate Metabolism of Tubers

Once harvested, potato tubers are subject to disease, shrinkage and sprouting during storage. To avoid these losses the storage temperature is reduced to 35–40° F. However, at reduced temperatures, the starch in the tubers undergoes conversion to sugar, termed "cold sweetening", which reduces the commercial and nutritional value of the tuber. Two enzymes are critical for the cold sweetening process: acid invertase and UDP-glucose pyrophosphorylase. Zrenner, R., et al., 1996, Planta 198, 246–252 and Spychalla, J. P., et al., 1994, J. Plant Physiol. 144, 444–453, respectively. The sequence of potato acid invertase is found in EMBL database Accession No. X70368 (SEQ ID NO. 1) and the sequence of the potato UDP Glucose pyrophosphorylase is reported be Katsube, T. et al., 1991, Biochem. 30, 8546–8551. Accordingly, the present embodiment of the invention provides for a method of preventing cold sweetening by the interruption of the acid invertase or the UDP glucose phosphorylase gene by introduction of a frameshift, one or more in-frame termination codons or by interruption of the promoter.

EXAMPLE 3

Reduction in Post Harvest Browning Due to PPO

Polyphenol oxidase (PPO) is the major cause of enzymatic browning in higher plants. PPO catalyzes the conversion of monophenols to o-diphenols and of o-dihydroxyphenols to o-quinones. The quinone products then polymerize and react with amino acid groups in the cellular proteins, which results in discoloration. The problem of PPO induced browning is routinely addressed by the addition of sulfites to the foods, which has been found to be associated with some possible health risk and consumer aversion. PPO normally functions in the defense of the plant to pathogens or insect pests and, hence, is not essential to the viability of the plant. Accordingly, the present embodiment of the invention provides for a method of preventing enzymatic browning by the interruption of the PPO gene by introduction of a frameshift, one or more in-frame termination codons or by interruption of the promoter in apple, grape, avocado, pear and banana.

The number of PPO genes in the genome of a plant is variable; in tomatoes and potatoes PPO forms a multigene family. Newman, S. M., et al., 1993, Plant Mol. Biol. 21, 1035–1051, Hunt M. D., et al., 1993, Plant Mol. Biol. 21, 59–68; Thygesen, P. W., et al., 1995, Plant Physiol. 109, 525–531. The grape contains only a single PPO gene. Dry, I. B., et al., 1994, Plant Mol. Biol., 26, 495–502. When the plant species of interest contains multiple copies of PPO genes it is essential that the PPO gene that is normally expressed in the commercial product be interrupted. For example, only one PPO gene is expressed in potatoes of harvestable size, which gene is termed POT32 and its sequence is deposited in GENBANK accession No. U22921 (SEQ ID NO. 2), which sequence is incorporated by reference. The other potato PPO isozymes have been sequenced and the sequences deposited so that one skilled in the art can design a MDON that specifically inactivates POT32.

EXAMPLE 4

Reduction of Lignin in Forage Crops and Wood Pulp

Lignin is a complex heterogeneous aromatic polymer, which waterproofs higher plants and strengthens their cell walls. Lignin arises from the random polymerization of free radicals of phenylpropanoid monolignins. Lignins pose a serious problem for the paper industry because their removal from wood pulp involves both monetary and environmental costs. Similarly, the lignin content of forage crops limits their digestibility by ruminants. Indeed, naturally occurring mutations, termed "brownmid-rib" in sorghum, Porter, K S, et al., 1978, Crop Science 18, 205–218, and *maize,* Lechtenberg, V. L., et al., 1972, Agron. J. 64, 657–660, have been identified as having reduced lignin content and tested as feed for cattle.

The brown mid-rib mutation in *maize* involves the O-methyl transferase gene. Vignol, F., et al., 1995, Plant Cell 7, 407–416. The O-methyltransferase genes of a number of plant species have been cloned: Burgos, R. C., et al., 1991, Plant Mol. Biol. 17, 1203–1215 (aspen); Gowri, G., et al., 1991, Plant Physiol. 97, 7–14 (alfalfa, *Medicago sativa*) and Jaeck, F., et al., 1992, Mol. Plant-Microbe Interact. 4, 294–300 (tobacco) (SEQ ID No. 3 and SEQ ID No. 4). Thus, one aspect of the present embodiment is the interruption of the O-methyltransferase gene to reproduce a brown mid-rib phenotype in any cultivar of *maize* or sorghum and in other species of forage crops and in plants intended for the manufacture of wood pulp.

A second gene that is involved in lignin production is the cinnamyl alcohol dehydrogenase (CAD) gene, which has been cloned in tobacco. Knight, M. E., 1992, Plant Mol. Biol. 19, 793–801 (SEQ ID No. 5 and SEQ ID No. 6). Transgenic tobacco plants making a CAD antisense transcript have reduced levels of CAD and also make a lignin that is more readily extractable, apparently due to an increase in the ratio of syringyl to guaiacyl monomers and to the increased incorporation of aldehyde monomers relative to alcohol residues. Halpin, C., et al., 1994, The Plant Journal 6, 339–350. Accordingly, an embodiment of the invention is the interruption of the CAD gene of forage crops such as alfalfa, *maize,* sorghum and soybean and of paper pulp trees such as short-leaf pine (*Pinus echinata*) long-leaf pine (*Pinus palustris*) slash pine (*Pinus elliottii*), loblolly pine (*Pinus taeda*), yellow-poplar (*Liriodendron tulipifera*) and cotton wood (*Populus* sp.) by introduction of a frameshift, one or more in-frame termination codons or by interruption of the promoter.

EXAMPLE 5

The Reduction in Unsaturated and Polyunsaturated Lipids in Oil Seeds

The presence of unsaturated fatty acids, e.g., oleic acid, and polyunsaturated fatty acids, e.g., linoleic and linolenic acids, in vegetable oil from oil seeds such as rape, peanut, sunflower and soybean causes the oils to oxidize, on prolonged storage and at high temperatures. Consequently, vegetable oil is frequently hydrogenated. However, chemical hydrogenation causes transhydrogenation, which produces non-naturally occurring stereo-isomers, which are believed to be a health risk.

Fatty acid synthesis proceeds by the synthesis of the saturated fatty acid on an acyl carrier protein (ACP) followed by the action of desaturases that remove the hydrogen pairs. Consequently, it would be desirable to inhibit the activity of these desaturase enzymes in oil seeds.

The first enzyme in the synthesis of oleic acid is stearoyl-ACP desaturase (EC 1.14.99.6). The stearoyl-ACP desaturases from safflower and castor bean have been cloned and sequenced. Thompson, G. A., et al., 1991, Proc. Natl. Acad. Sci. 88, 2578–2582 (SEQ ID No. 7); Shanklin, J., & Somerville, C., 1991, Proc. Natl. Acad. Sci. 88, 2510–2514 (SEQ ID No. 8); Knutzon, D. S., et al., 1991, Plant Physiology 96, 344–345. Accordingly, one embodiment of the present invention is the interruption of the stearoyl-ACP desaturase gene of oil seed crops such as soybean, safflower, sunflower, soy, *maize* and rape by introduction of a frameshift, one or more in-frame termination codons or by interruption of the promoter.

A second enzyme that can be interrupted according to the present invention is ω-3 fatty acid desaturase (ω-3 FAD) the enzyme that converts linoleic acid, a diene, to linolenic acid, a triene. There are two ω-3 FAD isozymes in *Arabidopsis thaliana* and, those skilled in the art expect, in most other plants. One isozyme is specific for plastids and is the relevant isozyme for the synthesis of the storage oils of seeds. The other is microsome specific. The cloning of the *Arabidopsis thaliana* plastid ω-3 FAD is reported by Iba., K. et al., 1993, J. Biol. Chem. 268, 24099–24105 (SEQ ID No. 9). Accordingly an embodiment of the invention is the interruption of the plastid ω-3 FAD gene of oil seed crops such as soybean, safflower, sunflower, soy, *maize* and rape by introduction of a frameshift, an in-frame termination codon or by interruption of the promoter.

EXAMPLE 6

Inactivation of S Alleles to Permit Inbred Lines

Certain plant species have developed a mechanism to prevent self-fertilization. In these species, e.g., wheat and rice, there is a locus, termed S, which has multiple alleles. A plant that expresses an S allele cannot be fertilized by pollen expressing the same S allele. Lee, H-K., et al., 1994, Nature 367, 560–563; Murfett, J., et al., 1994, Nature 367, 563. The product of the S locus is an RNase. McClure, B. A., et al., 1989, Nature 342, 955–957. The product of the S locus is not essential for the plant. Accordingly, an embodiment of the invention is the interruption of genes of the S locus to permit the inbreeding of the plant by introduction of a frameshift, one or more in-frame termination codons or by interruption of the promoter.

EXAMPLE 7

Ethylene Insensitivity

Ethylene is a gaseous plant hormone that is involved in plant growth and development. An unwanted aspect of ethylene's action is the over-ripening of fruit, vegetables and the wilting of flowers that results in rotting and loss. The ethylene receptor of *Arabidopsis thaliana* has been cloned and is termed ETR-1. Chang, C., et al., 1993, Science 262, 539–544 (SEQ ID No. 10). A mutant, Cys→Tyr$^{65}$, results in a dominant insensitivity to ethylene. Transgenic tomato plants expressing the *Arabidopsis thaliana* mutant ETR-1 also showed an insensitivity to ethylene, indicating that the Cys→Tyr$^{65}$ mutation would be a dominant suppressor of ethylene action in most plant species. Accordingly one aspect of the present embodiment of the invention is the insertion of the Cys→Tyr$^{65}$ mutation into the ETR-1 gene so as to extend the life span of the mutated fruit vegetable or flower.

In a further aspect of the present embodiment, the preservation of the fruit or flower can be achieved by interrupting one of the genes that encode the enzymes for ethylene synthesis: namely 1-aminocyclopropane-1-carboxylic acid synthase (ACC synthase) and ACC oxidase. For this embodiment of the invention the amount of ethylene synthesis can be eliminated entirely, so that ripening is produced by exogenous ethylene or some amount of ethylene production can be retained so that the fruit ripens spontaneously, but a has a prolonged storage life. Accordingly, it is anticipated that the interruption of one allele of either the ACC synthase or the ACC oxidase gene can result in an useful reduction in the level of ethylene synthesis. Alternatively, the invention provides for the interruption of one allele along with the introduction of a mutation that results in a partial loss of activity in the uninterrupted allele.

The sequences of the *Arabidopsis thaliana* ACC synthase and ACC oxidase genes are reported in Abel., S., et al., 1995, J. Biol. Chem. 270, 19093–19099 (SEQ ID No. 12) and Gomez-Lim, M. A., et al., 1993, Gene 134,217–221 (SEQ ID No. 11), respectively, which are incorporated by reference in their entirety.

EXAMPLE 8

Reversion of Kanamycin Resistance

Recombinant DNA technology in plants allows for the introduction of genes from one species of plant and bacterial genes into a second species of plant. For example, Kinney, A. J., 1996, Nature Biotech. 14, 946, describes the introduction of a bay laural ACP-thioesterase gene into the rape seed to obtain a vegetable oil rich in lauric acid. Such transgenic plants are normally constructed using an antibiotic resistance gene, e.g., kanamycin resistance, which is coinserted into the transgenic plant as a selectable trait. The resultant transgenic plant continues to express the antibiotic resistance gene, which could result in large amounts of the resistance product and the gene entering the food supply and/or the environment, which introduction may represent an environmental or health risk. An embodiment of the invention obviates the risk by providing for the interruption of the kanamycin gene by introduction of a frameshift, one or more in-frame termination codons or by interruption of the promoter.

EXAMPLE 9

Modification of Storage Protein Amino Acid Content

Seeds and tubers contain a family of major storage proteins, e.g., patatins in potato and zeins in *maize*. The amino acid composition of such storage proteins is often poorly suited to the needs of the human and animals that depend on these crops, e.g., corn is deficient in lysine and methionine and potato is deficient in methionine. Accordingly, one embodiment of the invention is the mutation of a storage protein of a food crop to increase the amount of low abundance amino acids. Patatins are encoded by a multigene family which are characterized in Mignery, G. A., et al., 1988, Gene 62, 27–44, and the structure of zeins is reported by Marks, M. D., et al., 1985, J. Biol. Chem. 260, 16451459, both of which are hereby incorporated by reference. Alternatively, the anticodon of a methionine or lysine specific tRNA can be mutated to that of a more common amino acid.

EXAMPLE 10

The Use of MDON to Determine the Function of a Gene

The presently available techniques for the cloning and sequencing of tissue specific cDNAs allow those skilled in the art to obtain readily the sequences of many genes. There is a relative paucity of techniques for determining the function of these genes. In one embodiment of the invention, MDON are designed to introduce frameshilft or stop codons into the gene encoding a cDNA of unknown function. This allows for the specific interruption of the gene. Plants having such specific "knock-outs" can be grown and the effects of the knock-out can be observed in order to investigate the function of the unknown gene.

4.8 Fertile Plants of the Invention

The invention encompasses a fertile plant having an isolated selectable point mutation, which isolated selectable mutation is not a rare polymorphism, i.e., would not be found in population of about 10,000 individuals. As used herein a point mutation is mutation that is a substitution of not more than six contiguous nucleotides, preferably not more than three and more preferably one nucleotide or a deletion or insertion from one to five nucleotides and preferably of one or two nucleotides. As used herein an isolated mutation is a mutation which is not closely linked genetically to any other mutation, wherein it is understood that mutations that are greater than 100 Kb and preferably greater than 40 Kb and more preferably greater than 23 Kb are not closely linked.

BIOLISTIC WORKING EXAMPLES

In the following working examples the media and protocols found in Gelvin, S. B., et al., (eds) 1991, *PLANT*

*MOLECULAR BIOLOGY MANUAL* (Kluwer Acad. Pub.) were followed. Gold particles were coated with MDON according the following protocol. The microprojectiles are first prepared for coating, then immediately coated with the chimeraplast. To prepare the microprojectiles, suspend 60 mg of gold particles in 1 ml of 100% ethanol (see Note 4). Sonicate the suspension for three, 30 s bursts to disperse the particles. Centrifuge at 12,000×g for 30 s, discard supernatant. Add 1 ml of 100% ethanol, vortex for 15 s, centrifuge at 12,000×g for 5 min, then discard the supernatant. A 25 µl suspension of washed gold particles (1.0 µm diameter, 60 mg/ml) in $H_2O$ are slowly vortexed, to which 40 µl MDON (50 µg/ml), 75 µl of 2.5 M $CaCl_2$, 75 µl 0.1M spermidine are sequentially added. All solutions are ice cold. The completed mixture is vortexed for a further 10 min and the particles are allowed to settle at room temperature for a further 10 min. The pellet is washed in 100% EtOH and resuspended in 50 µl. of absolute ethanol. Biolistic delivery is performed using a Biorad Biolistic gun with the following settings: tank pressure 1100 psi, rupture disks ×2 breaking at 900 psi, particle suspension volume 5 µl.

NT-1 (Tobacco), a Dicot Cell Suspension:

Lawns of NT-1 of approximately 5 cm diameter, containing 5 million cells, were grown for 3 days on standard media at 28° C. Gold particles were coated with ALS-1 or ALS-2 and were shot as above. The cells were cultured a further 2.5 days, suspended and transferred to solid medium supplemented with 15–50 ppb chlorsulfuron (GLEAM™). Resistant colonies emerged after 7–14 days.

The sequences of the MDON used are as follows: (The nucleotides not homologous with the target gene are underlined and bold. Lower case letters denote 2'-Omethyl ribonucleotides.)

```
ALS-1
 TGCGCG-guccaguucaCGTTGcauccaacuaT (SEQ ID No. 13)
T                                 T
T                                 T
 TCGCGC CAGGTCAAGTGCAACGTAGGATGATT
     3' 5'

ALS-2
 TGCGCG-guccaguucaCGATGcauccaacuaT (SEQ ID No. 14)
T                                 T
T                                 T
 TCGCGC CAGGTCAAGTGCTACGTAGGATGATT
     3' 5'
```

ALS-1 and ALS-2 have single base mismatches with the ALS gene at the second nucleotide of the $Pro^{197}$ (CCA) codon: ALS-1 is CAA and ALS-2 is CTA. Following PCR amplfication and sequencing of the gene of the ALS-1 and ALS-2 transmutated, resistant cell lines, a mutation was in the targeted codon which was found to be Thr (ACA) and Ser (TCA), respectively. The observed mutation was shifted one nucleotide 5' of the location that would have been expected based on the action of MDON in mammalian cells on the coding strand and one nucleotide 3' of the expected location on the non-coding strand. A total of 3 ALS-1 and 5 ALS-2 transmutants having these mutations were identified. No resistant calli were obtained from ALS-1 DNA treated cells.

For selection of chlorsulfuron resistant cells, cells were transferred from each bombarded plate to 15 ml containing 5 ml of liquid CSM 2 d after bombardment. The tubes were inverted several times to disperse cell clumps. The cells were then transferred to solidified CSM medium containing 15 ppb chorsulfuron (Dupont, Wilmington, Del.). After approximately 3–5 wk, actively growing cells (raised, light colored colonies) are selected and transferred to solidified CSM containing 50 ppb chlorsulfuron. Three to four weeks later, actively growing cells are selected, then transferred to solidified CSM containing 200 ppb chlorsulfuron. Cells that survive this treatment are then analyzed.

Media

1. NT-1 cell suspension medium (CSM): Murashige and Skoog salts (Gibco BRL, Grand Island, N.Y.), 500 mg/l MES, 1 mg/l thiamine, 100 mg/l myoinositol, 180 mg/l $KH_2PO_4$, 2.21 mg/L 2,4-diclorophenoxyacetic acid (2,4-D), 30 g/L sucrose. Adjust pH to 5.7 with 1M KOH or HCl and autoclave. For solidified medium add 8 g/l Agar-agar (Sigma, St. Louis, Mo.) prior to autoclaving.
2. Plating out medium (POM): 80% (v/v) CSM, 0.3M mannitol, 20% (v/v) supernatant from the initial centrifugation of the NT-1 cell suspension prior to protoplast isolation.

Tobacco Leaf, a Dicot:

*Nicotiana tabacum* v. Samsun leaf disks were co-transformed by *Agrobacterium tumefaciens* LBA 4404 harboring bin 19-derived plasmids containing a nptII expression cassette containing two genes: a gene for kanamycin resistance and one of two mutants of a gene encoding a Green Fluorescence Protein (GFP, Chui, W., 1996, Current Biol. 6, 325–330). Neither mutant GFP gene produces a GFP product. The mutants contain either a G→T substitution in the sixth codon resulting in a stop codon or a deletion of one nucleotide at the same position, which are termed, respectively, G-stop and G-Δ. After culture on selective MS 104 medium, leaves were recovered and the presence of a GFP gene confirmed by northern blot. Sequence of first eight codons of GFP:

```
                               (SEQ ID No. 15)
  GFP      ATG GTG AGC AAG GGC GAG GAG CTG (SEQ ID No. 16)
  C-stop   --------------------T-----------

(SEQ ID No. 17)
  G-Δ      --------------------AGG AGC TGT
```

The sequences of the MDON used were as follows: (The nucleotides not homologous with G-stop are underlined and bold. Lower case letters denote 2'-Omethyl ribonucleotides.)

```
GFP-1
 TGCGCG-cacucguuccCGCTCcucgacaaguT (SEQ ID No. 18)
T                                 T
T                                 T
 TCGCGC GTGAGCAAGGGCGAGGAGCTGTTCAT
     3' 5'

GFP-2
 TGCGCG-acucguucccGAGCCucgacaagugT (SEQ ID NO. 19)
T                                 T
T                                 T
 TCGCGC TGAGCAAGGGCTCGGAGCTGTTCACT
     3' 5'
```

Leaf disks of the G-stop and G-Δ transgenic plants were incubated on MS 104 selective media and G-1 or G-1 introduced biolistically by two successive deliveries as above. Approximately 10 days after the introduction of the MDON, calli exhibiting GFP-like fluorescence were seen in the G-1 and G-2 treated cultures of both the G-stop and G-Δ leaf disks. Larger and more rapidly growing callusing pieces were subdivided by scalpel to obtain green fluorescent cell-enriched calli. The fluorescent phenotype remained stable for the total period of observation, about 30 days. The presence of green fluorescent cells in the G-1 treated G-stop culture indicates that G-1 does not cause mutations exclusively one base 5' of the mismatched nucleotide.

Green fluorescence was observed using a standard FITC filter set using an IMT-2 Olympus microscope.

ELECTROPORATION WORKING EXAMPLE

Conversion of GFP in Tobacco Mesophyll Protoplasts

Plant Material
1. Tobacco plant transformant (Delta6) harboring a deletion mutant of GFP.
2. Leaves were harvested from 5 to 6-week-old in vitro-grown plantlets Protoplast Isolation
1. Basically followed the procedure of Gallois, et al., 1996, Electroporation of tobacco leaf protoplasts using plasmid DNA or total genomic DNA. Methods in Molecular Biology, Vol. 55: Plant Cell Electroporation and Electrofusion Protocols Edited by: J. A. Nickoloff Humana Press Inc., Totowa, N.J. pp. 89–107.
2. Enzyme solution: 1.2% cellulase R-10 "Onozuka" (Karlan, Santa Rosa, Calif.), 0.8% macerozyme R-10 (Karlan, Santa Rosa, Calif.), 90 g/l mannitol, 10 mM MES, filter sterilize, store in 10 ml aliquots at −20° C.
3. Leaves were cut from the mid-vein out every 1–2 mm. They were then placed abaxial side down in contact with 10 ml of enzyme solution in a 100×20 mm petri plate. A total of 1 g of leaves was placed in each plate.
4. The plates were incubated at 25° C. in the dark for 16 hr.
5. The digested leaf material was pipetted and sieved through a 100 μm nylon screen cloth (Small Parts, Inc., Miami Lakes, Fla.). The filtrate was then transferred to a centrifuge tube, and centrifuged at 1000 rpm for 10 min. All centrifugations for this protocol were done at these conditions.
6. The protoplasts collected in a band at the top. The band of protoplasts was then transferred to a clean centrifuge to which 10 ml of a washing solution (0.4 M sucrose and 80 mM KCl) was added. The protoplasts were gently resuspended, then centrifuged.
7. Repeated step 6 twice.
8. After the last wash, the protoplast density was determined by dispensing a small aliquot onto a hemocytometer. Resuspend the protoplasts to a density of $1 \times 10^6$ protoplasts/ml in eletroporation buffer (80 mM KCl, 4 mM $CaCl_2$, 2 mM potassium phosphate, pH 7.2, 8% mannitol, autoclave. The protoplasts were allowed to incubate at 8° C. for 2 hr.
9. After 2 hr, 0.3 ml ($3 \times 10^5$ protoplasts) were transferred to each 0.4 cm cuvette, then placed on ice. GFP-2 (0.6–4 μg/mL) was added to each cuvette except for an unelectroporated control. The protoplasts were electroporated (250V, capacitance 250 μF, and time constant 10–14 ms).
10. The protoplasts were allowed to recover for 10 min on ice, then transferred to petri plates (100×20 mm). After 35 min, 10 ml of POM, see above, was added to each plate. The plates were transferred to the dark at 25° C. for 24 hr, then transferred to the light.
11. The protoplast cultures were then maintained according to *Gallois supra*.

Fluorescence Microscopy
1. Under UV light, we observed 8 GFP converted protoplasts out of $3 \times 10^5$ protoplasts.

---

We claim:

1. A method of making a localized mutation in a plant cell to an ALS gene causing the plant cell to be herbicide resistant comprising the steps of:
   (a) adhering to a particle a recombinagenic oligonucleobase, which contains a first homologous region which has a sequence identical to the sequence of at least 6 base pairs of a first fragment of the ALS gene and a second homologous region which has a sequence identical to the sequence of at least 6 base pairs of a second fragment of the ALS gene, and an intervening region which contains at least 1 nucleobase heterologous to the ALS gene, which intervening region connects the first homologous region and the second homologous region;
   (b) introducing the particle into a cell of a population of plant cells;
   (c) identifying a cell of the population of plant cells having a mutation located between the first and second fragments of the ALS gene.

2. The method of claim 1, wherein the recombinagenic oligonucleobase is a mixed duplex oligonucleotide (MDON) and each of the homologous regions contains an RNA segment of at least 6 RNA-type nucleotides.

3. The method of claim 2, wherein the intervening region is at least 3 nucleotides in length.

4. The method of claim 2, which further comprises the step of culturing the identified cell so that a plant is generated.

5. The method of claim 2, wherein the adhering step is performed in a solution comprising 1.1–1.4 M NaC 1 and 18–22 μM spermidine and at least 14 μg/ml mixed duplex oligonucleotide (MDON).

6. The method of claim 1, wherein the plant cell is a *maize*, wheat, rice or lettuce cell.

7. The method of claim 1, wherein the plant cell is a potato, tomato, canola, soybean or cotton cell.

8. The method of claim which further comprises making seeds from the plant or from progeny of the plant.

9. A method of making a localized mutation in an ALS gene in a plant cell having a cell wall comprising the steps of:
   (a) perforating the cell walls of a population of plant cells;
   (b) introducing a recombinagenic oligonucleobase, which contains a first homologous region which has a sequence identical to the sequence of at least 6 base pairs of a first fragment of the ALS gene and a second homologous region which has a sequence identical to the sequence of at least 6 base pairs of a second fragment of the ALS gene, and an intervening region which contains at least 1 nucleobase heterologous to the ALS gene, which intervening region connects the first homologous region and the second homologous region;
   (c) identifying a cell of the population of plant cells having a mutation located between the first and second fragments of the ALS gene.

10. The method of claim 9, wherein the recombinagenic oligonucleobase is a mixed duplex oligonucleotide (MDON) and each of the homologous regions contains an RNA segment of at least 6 RNA-type nucleotides.

11. The method of claim 10, which further comprises the step of culturing the identified cell so that a plant is generated.

12. The method of claim 10, wherein the sequence of the ALS gene between the first and the second fragments differs from the sequence of the intervening region of the mixed duplex oligonucleotide (MDON) at a mismatched nucleotide and the mutation of the ALS gene is located adjacent to the mismatched nucleotide.

13. The method of claim 10, wherein the sequence of the ALS gene between the first and the second fragments differs from the sequence of the mutator segment of the mixed duplex oligonucleotide (MDON) at a mismatched nucleotide and the mutation of the ALS gene is located at the mismatched nucleotide.

14. The method of claim 9, wherein the plant cell is a *maize,* wheat, rice or lettuce cell.

15. The method of claim 9, wherein the plant cell is a potato, tomato, canola, soybean or cotton cell.

16. The method of claim 11, which further comprises making seeds from the plant of from progeny of the plant.

* * * * *

SEQUENCE LISTING

```
<160> NUMBER OF SEQ ID NOS: 19

<210> SEQ ID NO 1
<211> LENGTH: 2063
<212> TYPE: DNA
<213> ORGANISM: Solanum tuberosum
<220> FEATURE:
<221> NAME/KEY: CDS
<222> LOCATION: (3)...(1907)

<400> SEQUENCE: 1
agtaccattc cagttatgac ccggaaaact ccgcctccca ttacacattc ctcccggatc      60
aacccgattc cggccaccgg aagtccctta aaatcatctc cggcattttc ctctcctctt     120
tccttttgct ttctgtagcc ttctttccga tcctcaacaa ccagtcaccg gacttgcaga     180
gtaactcccg ttcgccgccg ccgtcaagag gtgtttctca gggagtctcc gataagactt     240
ttcgagatgt cgtcaatgct agtcacattt cttatgcgtg gtccaatgct atgcttagct     300
ggcaaagaac tgcttaccat tttcaacctc aaaaaaattg gatgaacgat cctaatggtc     360
cattgtacca caagggatgg tatcatcttt tttatcaata caatccagat tcagctattt     420
ggggaaatat cacatgggc catgccgtat ccaaggactt gatccactgg ctctacttgc     480
cttttgccat ggttcctgat caatggtacg atattaacgg tgtctggact gggtccgcct     540
ccatcctacc cgatggtcag atcatgatgc tttataccgg tgtctctgat gattatgtac     600
```

-continued

```
aagtgcaaaa tcttgcgtac cccaccaact tatctgatcc tctccttcta gactgggtca        660
agtacaaagg caacccggtt ctggttcctc cacccggcat tggtatcaag gactttagag        720
acccgaccac tgcttggacc ggaccccaaa atgggcaatg cttttaaca atcgggtcta         780 agattggtaa acgggtatt gcacttgttt atgaaacttc caacttcaca agctttaagc         840
tattggatga agtgctgcat gcggttccgg gtacgggtat gtgggagtgt gtggactttt        900
acccggtatc gactgaaaaa acaaacgggt tggacacatc atataacggc ccgggtgtaa        960
agcatgtgtt aaaagcaagt ttagatgaca ataagcaaga tcactatgct attgggacgt       1020
atgacttgac aaagaacaaa tggacacccg ataacccgga attggattgt ggaattgggt       1080
tgaagctgga ttatgggaaa tattatgcat caaagacatt ttatgacccg aagaaacaac       1140
gaagagtact gtgggatgg attggggaaa ctgatagtga atctgctgac ctgcagaagg        1200
gatgggcatc tgtacagagt attccaagga cagtgcttta cgacaagaag acaggacac        1260 atctacttca gtggccagtt gaagaaattg aaagcttaag agtgggtgat cctattgtta       1320
agcaagtcaa tcttcaacca ggttcaattg agctactcca tgttgactca gctgcagagt       1380
tggatataga agcctcattt gaagtggaca agtcgcgct ccagggaata attgaagcag        1440
atcatgtagg tttcagctgc tctactagtg gaggtgctgc tagcagaggc atttgggac       1500 catttggtgt cgttgtaatt gctgatcaaa agctatctga gctaacgcca gtttacttct       1560
acatttctaa aggagctgat ggtcgagctg agactcactt ctgtgctgat caaactagat       1620
cctcagaggc tccgggagtt gctaaacaag tttatggtag ttcagtaccc gtgttagacg       1680
gtgaaaaaca ttcgatgaga ttattggagg accactcaat tgtggagagc tttgcccaag       1740
gaggaagaac agtcataaca tcgcgaattt acccaacaaa ggcagtgaat ggagcagcac       1800
gactcttcgt tttcaacaat gccacagggg ctagcgtgac tgcttccgtc aagatttggt       1860
cacttgagtc ggctaatatt cgatccttcc ccttgcaaga cttgtaattc atcaagccat       1920
atcttcttca ttcttttttt catttgaagg ttatttcacc gatgtcccat caagaaaggg       1980
aagagaggga gaatatgtag tgttatactc tacttattcg ccattttagt gattttttcta      2040 ctggactttt gctattcgca aaa                                                2063
```

<210> SEQ ID NO 2
<211> LENGTH: 1958
<212> TYPE: DNA
<213> ORGANISM: Solanum tuberosum
<220> FEATURE:
<221> NAME/KEY: CDS
<222> LOCATION: (22)...(1815)

<400> SEQUENCE: 2

```
tcttttgcgt tttgagcaat aatggcaagc ttgtgcaata gtagtagtac atctctcaaa         60 actccttttta cttcttcctc cacttctttta tcttccactc ctaagccctc tcaacttttc     120
atccatggaa aacgtaacca aatgttcaaa gtttcatgca aggttaccaa taataacggt       180
gaccaaaacc aaaacgttga aacaaattct gttgatcgaa gaaatgttct tcttggctta       240
ggtggtcttt atggtgttgc taatgctata ccattagctg catccgctgc tccagctcca       300
cctcctgatc tctcgtcttg tagtatagcc aggattaacg aaaatcaggt ggtgccgtac       360
agttgttgcg cgcctaagcc tgatgatatg gagaaagttc cgtattacaa gttcccttct       420
atgactaagc tccgtgttcg tcagcctgct catgaagcta atgaggagta tattgccaag       480
tacaatctgg cgattagtcg aatgaaagat cttgataaga cacaaccttt aaaccctatt       540
```

-continued

```
ggttttaagc aacaagctaa tatacattgt gcttattgta acggtgctta tagaattggt      600
ggcaaagagt tacaagttca taattcttgg ctttcttcc cgttccatag atggtacttg       660
tacttccacg agagaatcgt gggaaaattc attgatgatc aactttcgc tttaccatat       720
tggaattggg accatccaaa aggtatgcgt tttcctgcca tgtatgatcg tgaagggact      780
tcccttttcg atgtaacacg tgaccaaagt caccgaaatg agcagtaat cgatcttggt       840
tttttcggca atgaagttga aacaactcaa ctccagttga tgagcaataa tttaacacta     900
atgtaccgtc aaatggtaac taatgctcca tgtcctcgga tgttctttgg cgggccttat     960
gatctcgggg ttaacactga actcccggga actatagaaa acatccctca cggtcctgtc    1020
cacatctggt ctggtacagt gagaggttca actttgccca atggtgcaat atcaaacggt   1080
gagaatatgg gtcattttta ctcagctggt ttggacccgg ttttcttttg ccatcacagc   1140
aatgtggatc ggatgtggag cgaatggaaa gcgacaggag ggaaaagaac ggatatcaca   1200
cataaagatt ggttgaactc cgagttcttt ttctatgatg aaaatgaaaa cccttaccgt    1260
gtgaaagtca gagactgttt ggacacgaag aagatgggat acgattacaa accaattgcc    1320
acaccatggc gtaacttcaa gcccttaaca aaggcttcag ctggaaaagt gaatacagct    1380
tcacttccgc cagctagcaa tgtattccca ttggctaaac tcgacaaagc aatttcgttt    1440
tccatcaata ggccgacttc gtcaaggact caacaagaga aaaatgcaca agaggagatg    1500
ttgacattca gtagcataag atatgataac agagggtaca taaggttcga tgtgttttcg    1560
aacgtggaca taatgtgaa tgcgaatgag cttgacaagg cggagtttgc ggggagttat     1620
acaagtttgc cacatgttca tagagctggt gagactaatc atatcgcgac tgttgatttc    1680
cagctggcga taacggaact gttggaggat attggttttgg aagatgaaga tactattgcg   1740
gtgactctgg tgccaaagag aggtggtgaa ggtatctcca ttgaaggtgc gacgatcagt    1800
cttgcagatt gttaattagt ctctattgaa tctgctgaga ttcactttg atggatgatg     1860
ctctgttttt gttttcttgt tctgtttttt cctctgttga aatcagcttt gttgcttgat    1920
ttcattgaag ttgttattca agaataaatc agttacaa                            1958
```

<210> SEQ ID NO 3
<211> LENGTH: 1460
<212> TYPE: DNA
<213> ORGANISM: Nicotiana tabacum
<220> FEATURE:
<221> NAME/KEY: CDS
<222> LOCATION: (84)...(1178)

<400> SEQUENCE: 3

```
tctgtttctt caactcacct taatttgccc aattgagtca ttgtaaaatc tgaaacagaa      60
ccaagagaga agagaaaaaa aatatgggtt caacaagcca gagccagagt aagagtctaa    120
ctcacacaga agacgaagcg ttcttatttg ccatgcaatt ggctagtgct tctgtacttc    180
ctatggtcct aaaatcagcg ttagaacttg accttcttga actcatggct aaagctggtc    240
caggtgcagc catttctcct tctgaattag ctgctcagct ctcaacccag aacccagaag    300
cacccgttat tcttgatcgg atgcttaggc tacttgctac ttactctgtt ctcaattgta    360
ctcttagaac actgtctgat ggcagtgttg agaggcttta tagtctggct ccggtttgta    420
agttcttgac taagaatgct gatggtgttt ctgttgcccc acttttgctt atgaatcaag    480
ataaagttct tatggagagc tggtaccact taaaagatgc agtactagat ggtggaatcc    540
cattcaacaa ggcctatgga atgacagcat ttgagtacca tggcacagat ccaagattca    600
```

-continued

| | |
|---|---|
| acaaagttttt caaccgtggaa atgtctgatc actccactat gtcaatgaaa aagattcttg | 660 |
| aggactacaa aggatttgaa ggcctaaatt ccattgttga tgttggtggt ggaactggcg | 720 |
| ctactgttaa catgattgtc tccaaacatc cctctattaa gggtattaac tttgatttac | 780 |
| cacatgttat tggagatgct ccagcttacc ctggtgtcga gcacgttggt ggcgacatgt | 840 |
| ttgccagtgt gccaaaagca gatgccattt tcatgaagtg gatttgtcat gattggagcg | 900 |
| acgagcattg cctaaaattc ttgaagaatt gctatgaagc actacctgca aatgggaagg | 960 |
| tgataatagc ggagtgcata cttccagagg ccccagatac atcacttgca actaagaata | 1020 |
| cagtacatgt tgatattgtg atgttagcac ataacccagg aggcaaagaa aggactgaga | 1080 |
| aggaatttga ggctttggct aagggcgctg gttttactgg attcgcaagg cttgttgcgc | 1140 |
| ttacaacact tgggtcatgg aattcaacaa ataattaatc gattcctttg gaggattaag | 1200 |
| caatatactg ttcattttgc attttgaaat tctacttttc acagagtggc tttactgcga | 1260 |
| aataaaagaa atatatagct tttaccttga aaagatcaat gttcaagggg aaaaaaaaaa | 1320 |
| aggaagatga ataattgct ctcagaaaag cagtgtgtta ggaaaaagct ttttagctgg | 1380 |
| attttgaatt ttattgtatg tatttctgta atacacatgt attgaaggaa tactagttttt | 1440 |
| cgaccaatca tatttctttg | 1460 |

<210> SEQ ID NO 4
<211> LENGTH: 1418
<212> TYPE: DNA
<213> ORGANISM: Nicotiana tabacum
<220> FEATURE:
<221> NAME/KEY: CDS
<222> LOCATION: (59)...(1153)

<400> SEQUENCE: 4

| | |
|---|---|
| attccttcaa cttacccaat taagtcatcg aaaaatctga aacagaacta aaagtaaaat | 60 |
| gggttcaaca agcgagagcc agagtaacag tctcactcac acagaagacg aagctttctt | 120 |
| atttgccatg caattgtgta gtgcttctgt acttcctatg gtcctaaaat cagccgtaga | 180 |
| acttgaccctt cttgagctaa tggctaaggc tggtccaggt gcagctattt ctccttctga | 240 |
| attagctgct cagctctcaa ctcagaaccc agaagcacct gttatgcttg atcggatgct | 300 |
| taggctactt gcttcttact ctgttctcaa ttgtactctt agaacactgc ctgatagcag | 360 |
| tgttgagagg cttttatagtc tggctcccgt ctgtaagtac ttgactaaga atgctgatgg | 420 |
| tgtttctgtt gccccacttt tgcttatgaa tcaagataaa gttcttatgg agagctggta | 480 |
| ccacttaaaa gatgcagtac tagatggcgg aatcccattc aacaaagcct atggaatgac | 540 |
| agcatttgag taccatggca cagatccaag attcaacaaa gtgttcaacc gtggaatgtc | 600 |
| tgatcactcc actatgtcaa tgaagaagat tcttgaggac tacaaaggat ttgaaggcct | 660 |
| aaattccatt gttgatgttg gtggtggaac gggtgctact gttaacatga ttgtctctaa | 720 |
| atatccctct attaagggca ttaactttga tttgccacat gtaattggag atgctccaac | 780 |
| ttaccccggt gtcgagcacg ttggtggcga catgtttgct agtgtgccaa aagcagatgc | 840 |
| cattttcatg aagtggattt gtcatgattg gagcgatgag cattgcctaa aattcttgaa | 900 |
| gaattgctat gaagcactac ctgcaaatgg gaaggtgata attgcagagt gcatacttcc | 960 |
| agaggcccca gatacatcac ttgcaactaa gaatacagta catgttgata ttgttatgtt | 1020 |
| agcacataac ccaggaggca agaaaggac tgagaaggaa tttgaggctt tggctaaggg | 1080 |
| cgctggtttt actggattcg caaggcttgt tgcgcttaca acacttgggt catggaattc | 1140 |

```
aacaagtaat taatcgattc cttaatttga aggattaagc aatatactgt tcgttttgca    1200
tttggaaatt ctacttttct cagagtggct tgactgtgaa ataaaagaaa tatagctttt    1260
aacttgaaaa gattgatgtt caaaagaaaa aaggaagat gaaataattg ctctcagaaa     1320
agcaatgtgt taggaaaaag cttttttagc tggattttga attttactgt atgtatttct    1380
gttatacaca tgtattgaag gaatactagt tttcgacc                            1418

<210> SEQ ID NO 5
<211> LENGTH: 1419
<212> TYPE: DNA
<213> ORGANISM: Nicotiana tabacum
<220> FEATURE:
<221> NAME/KEY: CDS
<222> LOCATION: (92)...(1165)

<400> SEQUENCE: 5
atttctttct ctttcccttg aactgtgttt tcattttttc tgctctgaaa caatagtgtt      60
ttccttgtag attttaagtt aaaagaaaac catgggtagc ttggatgttg aaaaatcagc    120
tattggttgg gctgctagag acccttctgg tctactttca ccttatacct atactctcag    180
aaacacagga cctgaagatg tgcaagtcaa agttttgtat tgtggacttt gccacagtga    240
tcttcaccaa gttaaaaatg atcttggcat gtccaactac cctctggttc ctggacatga    300
agtggtggga aaagtagtgg aggtaggagc agatgtgtca aaattcaaag tgggggacac    360
agttggagtt ggattactcg ttggaagttg taggaactgt ggcccttgca agagagaaat    420
agagcaatat tgcaacaaga gatttggaa ttgcaatgat gtctacactg atggcaaacc     480
cacccaaggt ggttttgcta attctatggt tgttgatcaa actttgtgg tgaaaattcc     540 agagggtatg gcaccagaac aagcagcacc tctattatgt gctggcataa cagtatacag    600
tccattcaac cattttggtt taatcagag tggatttaga ggaggaattt tgggattagg     660
aggagttgga catatgggag tgaaaatagc aaaggcaatg gacatcatg ttactgtcat     720 tagttcttca aataagaaga gacaagaggc attggaacat cttggtgcag atgattatct    780
tgttagttca gacactgata aaatgcaaga agctgctgat tcacttgact atattattga    840
tactgtccct gttggccatc ctcttgaact ttatctttct ttgcttaaaa ttgatggcaa    900
acttatcttg atcggagtta tcaacacccc cttgcaattt atctctccca tggttatgct    960
cgggagaaag agcatcactg gaagctttat tggtagcatg aaggaaacag ggaaatgct    1020 agacttctgc aaagagaaag gtgtgacttc acagattgag atagtgaaaa tggattatat   1080
caacactgca atggagaggt tggagaaaaa tgatgtgagc tacagatttg ttgttgatgt   1140
tgctggaagc aagcttgacc agtaattgca caagaaaaac aacatggaat ggttcactat   1200
tatacaacaa ggctatgaga aaatagtac tcctcaactt tgatgtcatc tttgttacct    1260
ttgttttatt ttccacctgt attatcatat tggtggtcg agagtgacgt ttatgtatat   1320
tttctttctt caaaacaatc ttaaatgaat ttggatgttg gtgacgattt tgaaatatac   1380
caaccatgca aacttacttt ggtagaaaaa aaaaaaaaa                         1419

<210> SEQ ID NO 6
<211> LENGTH: 1398
<212> TYPE: DNA
<213> ORGANISM: Nicotiana tabacum
<220> FEATURE:
<221> NAME/KEY: CDS
<222> LOCATION: (88)...(1161)

<400> SEQUENCE: 6
```

-continued

```
attcctctttt cccttgaact gtgttttcgt ttttctgct ctaaaacaat cgtgtgttcc    60
ttctagattt taagtttaaa gaacatcatg ggtggcttgg aagttgagaa acaactatt   120
ggttgggctg ctagagaccc ttctggtgta ctttcacctt atacctatac tctcagaaac   180
acaggacctg aagatgtgga agtcaaagtt ttgtattgtg ggctctgtca cactgatctt   240
caccaagtta aaaatgatct tggcatgtcc aactaccctc tggttcctgg acatgaagtg   300
gtgggagaag tggtggaggt aggaccagat gtgtcaaaat tcaaagttgg ggacacagtt   360
ggagttggat tactcgttgg aagttgcagg aactgtggcc cttgcaagag agatatagag   420
caatattgca acaagaagat tggaactgc aatgatgtct acactgatgg caaacccacc   480
caaggtggtt ttgctaaatc catggttgtt gatcaaaagt ttgtggtgaa aattccagag   540
ggtatggcac cagaacaagc agcacctcta ttatgtgctg gtataacagt atacagtcca   600
ttgaaccatt ttggtttcaa acagagtgga ttaagaggag gaattttggg attaggagga   660
gtgggacaca tgggagtgaa aatagcaaag gcaatgggac atcatgttac tgtcattagt   720
tcttcaaata agaagagaca agaggcattg gaacatcttg gtgcagatga ttatcttgtc   780
agttcagaca ctgataaaat gcaagaggct tctgattcac ttgactatat tattgatact   840
gtccctgttg ccatcctct tgaacctat ctttctttgc ttaaaattga tggcaaactt   900
atcttgatgg gagttatcaa cacccccttg caatttatct ccccatggt tatgctcggg   960
agaaagagca tcacaggaag ctttattggt agcatgaagg aaacagagga aatgctagat  1020
ttctgcaaag agaaaggtgt gacttcacag attgagatag tgaaaatgga ttatatcaac  1080
actgcaatgg agaggttgga gaaaaatgat gtgaggtaca gatttgtggt tgatgttatt  1140
ggaagcaagc ttgaccagta attatattac acaagaaaaa caacatggaa tggttcacta  1200
ttatacaagg ctgtgagaat actaaacttt gatgtcgtct tttgtatcct tttgttttat  1260
ttgccacctg tatttctta tttggtgatc gagagtgacg tttatgtatt attttctttc  1320
ttcaaaacaa tttaatgtat gaatttggat gttggtgaaa aaaaaaaaa aaaaaaaaa  1380
aaaaaaaaaa aaaaaaaa                                                1398
```

<210> SEQ ID NO 7
<211> LENGTH: 1533
<212> TYPE: DNA
<213> ORGANISM: Carthamus tinctorius
<220> FEATURE:
<221> NAME/KEY: CDS
<222> LOCATION: (106)...(1296)

<400> SEQUENCE: 7

```
gctcacttgt gtggtggagg agaaaaacag aactcacaaa aagctttgcg actgccaaga    60
acaacaacaa caacaagatc aagaagaaga agaagaagat caaaaatggc tcttcgaatc   120
actccagtga ccttgcaatc ggagagatat cgttcgtttt cgtttcctaa gaaggctaat   180
ctcagatctc ccaaattcgc catggcctcc accctcggat catccacacc gaaggttgac   240
aatgccaaga agccttttca acctccacga gaggttcatg ttcaggtgac gcactccatg   300
ccaccacaga agatagagat tttcaaatcc atcgagggtt gggctgagca gaacatattg   360
gttcacctaa agccagtgga gaatgttggc aagcacaggg atttcttgcc ggaccctgca   420
tctgaaggat ttgatgaaca agtcaaggaa ctaagggcaa gagcaaagga gattcctgat   480
gattactttg ttgttttggt tggagatatg attacagagg aagccctacc tacttaccaa   540
acaatgctta ataccctaga tggtgtacgt gatgagactg gggctagcct tacgccttgg   600
```

```
gctgtctgga ctagggcttg acagctgaa gagaacaggc atggcgatct tctccacacc      660
tatctctacc tttctgggcg ggtagacatg aggcagatac agaagacaat tcagtatctc      720
attgggtcag gaatggatcc tcgtaccgaa acagcccct accttgggtt catctacaca      780
tcgtttcaag agcgtgccac atttgtttct cacggaaaca ccgccaggca tgcaaaggat      840
catggggacg tgaaactggc gcaaatttgt ggtacaatcg cgtctgacga aaagcgtcac      900
gagaccgctt atacaaagat agtcgaaaag ctattcgaga tcgatcctga tggcaccgtt      960
cttgcttttg ccgacatgat gaggaaaaag atctcgatgc ccgcacactt gatgtacgat     1020
gggcgtgatg acaacctctt cgaacatttc tcggcggttg cccaaagact cggcgtctac     1080
accgccaaag actacgccga catactgaaa tttctggtcg ggcggtggaa agtggcggat     1140
ttgaccggcc tatctggtga agggcgtaaa gcgcaagatt atgtttgcgg gttgccacca     1200
agaatcagaa ggctggagga gagagctcaa gggcgagcaa aggaaggacc tgttgttcca     1260 tcagctgga ttttcgatag acaggtgaag ctgtgaagaa aaaaaaacg agcagtgagt     1320 tcggtttctg ttggcttatt gggtagaggt taaaacctat tttagatgtc tgtttcgtgt     1380
aatgtggttt tttttcttct aatcttgaat ctggtattgt gtcgttgagt tcgcgtgtgt     1440
gtaaacttgt gtggctgtgg acatattata gaactcgtta tgccaatttt gatgacggtg     1500
gttatcgtct cccctggtgt ttttttattg ttt                                  1533

<210> SEQ ID NO 8
<211> LENGTH: 1643
<212> TYPE: DNA
<213> ORGANISM: Ricinus communis
<220> FEATURE:
<221> NAME/KEY: CDS
<222> LOCATION: (1)...(1239)

<400> SEQUENCE: 8
ttccggcaaa taacaaaaaa ccaaaagaaa aaggtaagaa aaaaaacaat ggctctcaag       60
ctcaatcctt tcctttctca aacccaaaag ttaccttctt tcgctcttcc accaatggcc      120
agtaccagat ctcctaagtt ctacatggcc tctaccctca gtctggttc taaggaagtt      180 gagaatctca agaagccttt catgcctcct cgggaggtac atgttcaggt tacccattct      240
atgccacccc aaaagattga gatctttaaa tccctagaca attgggctga ggagaacatt      300
ctggttcatc tgaagccagt tgagaaatgt tggcaaccgc aggattttt gccagatccc      360 gcctctgatg gatttgatga gcaagtcagg gaactcaggg agagagcaaa ggagattcct      420
gatgattatt ttgttgtttt ggttggagac atgataacgg aagaagccct tcccacttat      480
caaacaatgc tgaatacctt ggatggagtt cgggatgaaa caggtgcaag tcctacttct      540
tgggcaattt ggacaagggc atggactgcg gaagagaata gacatggtga cctcctcaat      600
aagtatctct acctatctgg acgagtggac atgaggcaaa ttgagaagac aattcaatat      660
ttgattggtt caggaatgga tccacggaca gaaaacagtc catacctttgg gttcatctat      720 acatcattcc aggaaaggc aaccttcatt tctcatggga acactgcccg acaagccaaa      780
gagcatggag acataaagtt ggctcaaata tgtggtacaa ttgctgcaga tgagaagcgc      840
catgagacag cctacacaaa gatagtgaa aaactctttg agattgatcc tgatggaact      900
gttttggctt ttgctgatat gatgagaaag aaaatttcta tgcctgcaca cttgatgtat      960 gatgccgag atgataatct ttttgaccac ttttcagctg ttgcgcagcg tcttggagtc     1020
tacacagcaa aggattatgc agatatattg gagttcttgg tgggcagatg gaaggtggat     1080
```

-continued

```
aaactaacgg gcctttcagc tgagggacaa aaggctcagg actatgtttg tcggttacct    1140
ccaagaatta gaaggctgga agagagagct caaggaaggg caaaggaagc acccaccatg    1200
cctttcagct ggattttcga taggcaagtg aagctgtagg tggctaaagt gcaggacgaa    1260
accgaaatgg ttagtttcac tcttttcat gcccatccct gcagaatcag aagtagaggt     1320
agaattttgt agttgctttt ttattacaag tccagtttag tttaaggtct gtggaaggga    1380
gttagttgag gagtgaattt agtaagttgt tgatactgtt gtgttcttgt gttgtcatga    1440
gtctgcttga tagtgagttt cttttgtttc cttttgttgt gttcttttat ctggtctctc    1500
tctctctctc tctctctttt tctcttatcc caagtgtctc aagtataata agcaaacgat    1560
ccatgtggca attttgatga tggtgatcag tctcacaact tgatcttttg tcttctattg    1620
gaaacacagc ctgcttgttt gaa                                            1643

<210> SEQ ID NO 9
<211> LENGTH: 2569
<212> TYPE: DNA
<213> ORGANISM: Arabidopsis thaliana
<220> FEATURE:
<221> NAME/KEY: exon
<222> LOCATION: (236)...(729)
<223> OTHER INFORMATION: Exon 1
<220> FEATURE:
<221> NAME/KEY: exon
<222> LOCATION: (1030)...(1119)
<223> OTHER INFORMATION: Exon 2
<220> FEATURE:
<221> NAME/KEY: exon
<222> LOCATION: (1201)...(1267)
<223> OTHER INFORMATION: Exon 3
<220> FEATURE:
<221> NAME/KEY: exon
<222> LOCATION: (1358)...(1450)
<223> OTHER INFORMATION: Exon 4
<220> FEATURE:
<221> NAME/KEY: exon
<222> LOCATION: (1530)...(1715)
<223> OTHER INFORMATION: Exon 5
<220> FEATURE:
<221> NAME/KEY: exon
<222> LOCATION: (1809)...(1889)
<223> OTHER INFORMATION: Exon 6
<220> FEATURE:
<221> NAME/KEY: exon
<222> LOCATION: (1993)...(2130)
<223> OTHER INFORMATION: Exon 7
<220> FEATURE:
<221> NAME/KEY: exon
<222> LOCATION: (2212)...(2403)
<223> OTHER INFORMATION: Exon 8

<400> SEQUENCE: 9
cacaccatca ctaataaatt tccttctcct ttcaagttgt agctaactta tataagacat     60
aagcgtgcga accagagaca gagatagaaa ttgagagacg ataagcaaag tagaaaacac    120
aagtttctct cacacacatt atctctttct ctattaccac cactcattca taacagaaac    180
ccaccaaaaa ataaaagag agacttttca ctctggggag agagctcaag ttctaatggc     240
gaacttggtc ttatcagaat gtggtatacg acctctcccc agaatctaca caacacccag    300
atccaatttc ctctccaaca acaacaaatt cagaccatca cttcttctt cttcttacaa     360 aacatcatca tctcctctgt cttttggtct gaattcacga gatggttca cgaggaattg    420 ggcgttgaat gtgagcacac cattaacgac accaatattt gaggagtctc cattggagga    480
agataataaa cagagattcg atccaggtgc gcctcctccg ttcaatttag ctgatattag    540
```

```
agcagctata cctaagcatt gttgggttaa gaatccatgg aagtctttga gttatgtcgt    600
cagagacgtc gctatcgtct ttgcattggc tgctggagct gcttacctca acaattggat    660
tgtttggcct ctctattggc tcgctcaagg aaccatgttt tgggctctct ttgttcttgg    720
tcatgactgg taaacttaaa acccctaact ttttcttgt tttctcctct gctttagtct     780
cctttagcct ttgatttggt caactttgga tgattccaaa gaaccaatcg aacaaattgg    840
tctttatcca tatctcttca aatagcttta ggacataatt ggtctctcag gtaacaagct    900
gtcattatca tcatactcat catgttgcta gtagaccaac ccaattggca actgtttgtt    960
ggttttgcaa ctgtgtaatc tgctttgaat tgtgaacaaa attattgatt tatgttgatt   1020
acattgcagt ggacatggta gtttctcaaa tgatccgaag ttgaacagtg tggtcggtca   1080
tcttcttcat tcctcaattc tggtcccata ccatggctgg tgagttttgc tttcagacca   1140
ttcttctcta aaaccacttg cagaatctca tcttcttcat gtaaaaatat gactttgcag   1200
gagaattagt cacagaactc accaccagaa ccatggacat gttgagaatg acgaatcttg   1260
gcatcctgta agtcaaaaac gtatttttt ggttatcttg ttttagtcct gtggtgtttc    1320
ttagatgcag ttttattaac tgtttctgta actgcagatg tctgagaaaa tctacaatac   1380
tttggacaag ccgactagat tctttagatt tacactgcct ctcgtgatgc ttgcataccc   1440 ttctacttg gtaagaactc ctctatttgt tatggtaact taagctgcca caccaagtaa    1500 aaagctcat gtctattctt ctgtttcagt gggctcgaag tccggggaaa aagggttctc    1560
attaccatcc agacagtgac ttgttcctcc ctaaagagag aaaggatgtc ctcacttcta   1620
ctgcttgttg gactgcaatg gctgctctgc ttgtttgtct caacttcaca atcggtccaa   1680
ttcaaatgct caaactttat ggaattcctt actgggtaat gcgccgctgt tactcccctg   1740
tttcagcctg agcaatttgt gtattattc ctctgcctta ctcaaaaagg tttttatgtc    1800
aaatacagat aaatgtaatg tggttggact ttgtgactta cctgcatcac catggtcatg   1860
aagataagct tccttggtac cgtggcaagg taaaatacat attctctgct tccactgttc   1920
tttgactaca tcgctctttc ttttaaggtt aaagccaact ggtgtgtaaa tctcatgatt   1980
ctcccaaaac aggagtggag ttacctgaga ggaggactta caacattgga tcgtgactac   2040
ggattgatca ataacatcca tcatgatatt ggaactcatg tgatacatca tcttttcccg   2100
cagatcccac attatcatct agtagaagca gtaagtaaat tgaaagtaaa gactgtttgt   2160
gtttttggtg ttcatgctag tttccctgac tcttgctcca ctgttatgca gacagaagca   2220
gctaaaccag tattagggaa gtattacagg gagcctgata agtctggacc gttgccatta   2280
catttactgg aaattctagc gaaaagtata aagaagatc attacgtgag cgacgaagga    2340
gaagttgtat actataaagc agatccaaat ctctatggaa ggtcaaagt aagagcagat    2400 tgaaatgaag caggcttgag attgaagttt tttctatttc agaccagctg attttttgct   2460
tactgtatca atttattgtg tcacccacca gagagttagt atctctgaat acgatcgatc   2520
agatggaaac aacaaatttg tttgcgatac tgaagctata tataccata               2569
```

<210> SEQ ID NO 10
<211> LENGTH: 3879
<212> TYPE: DNA
<213> ORGANISM: Arabidopsis thaliana
<220> FEATURE:
<221> NAME/KEY: exon
<222> LOCATION: (780)...(1685)
<223> OTHER INFORMATION: Exon 1
<220> FEATURE:
<221> NAME/KEY: exon
<222> LOCATION: (1761)...(2129)
<223> OTHER INFORMATION: Exon 2
<220> FEATURE:
<221> NAME/KEY: exon
<222> LOCATION: (2207)...(2461)
<223> OTHER INFORMATION: Exon 3
<220> FEATURE:
<221> NAME/KEY: exon
<222> LOCATION: (2544)...(2671)
<223> OTHER INFORMATION: Exon 4
<220> FEATURE:
<221> NAME/KEY: exon
<222> LOCATION: (2762)...(2959)
<223> OTHER INFORMATION: Exon 5
<220> FEATURE:
<221> NAME/KEY: exon
<222> LOCATION: (3088)...(3448)
<223> OTHER INFORMATION: Exon 6

<400> SEQUENCE: 10

```
aaagatagta tttgttgata aatatgggga tatttatcct atattatctg tattttctt      60
accattttta ctctattcct ttatctacat tacgtcatta cactatcata agatatttga    120
atgaacaaat tcatgcaccc accagctata ttacccttt ttattaaaaa aaacatctg     180
ataataataa caaaaaaatt agagaaatga cgtcgaaaaa aaagtaaga acgaagaaga    240
agtgttaaac ccaaccaatt ttgacttgaa aaaaagcttc aacgctcccc tttctcctt    300
ctccgtcgct ctccgccgcg tcccaaatcc ccaattcctc ctcttctccg atcaattctt   360
cccaagtaag cttcttcttc ctcgattctc tcctcagatt gtttcgtgac ttctttatat   420
atattcttca cttccacagt tttcttctgt tgttgtcgtc gatctcaaat catagagatt   480
gattaaccta attggtcttt atctagtgta atgcatcgtt attaggaact ttaaattaag   540
atttaatcgt taatttcatg attcggattc gaattttact gttctcgaga ctgaaatatg   600
caacctattt tttcgtaatc gttgtgatcg aattcgattc ttcagaattt atagcaattt   660
tgatgctcat gatctgtcta cgctacgttc tcgtcgtaaa tcgaagttga taatgctatg   720
tgtttgttac acaggtgtgt gtatgtgtga gagaggaact atagtgtaaa aaattcataa   780
tggaagtctg caattgtatt gaaccgcaat ggccagcgga tgaattgtta atgaaatacc   840
aatacatctc cgattcttc attgcgattg cgtattttc gattcctctt gagttgattt     900
actttgtgaa gaaatcagcc gtgtttccgt atagatgggt acttgttcag tttggtgctt   960
ttatcgttct ttgtggagca actcatctta ttaacttatg gactttcact acgcattcga  1020
gaaccgtggc gcttgtgatg actaccgcga aggtgttaac cgctgttgtc tcgtgtgcta  1080
ctgcgttgat gcttgttcat attattcctg atcttttgag tgttaagact cgggagcttt  1140
tcttgaaaaa taaagctgct gagctcgata gagaaatggg attgattcga actcaggaag  1200
aaaccggaag gcatgtgaga atgttgactc atgagattag aagcacttta gatagacata  1260
ctattttaaa gactacactt gttgagcttg gtaggacatt agctttggag gagtgtgcat  1320
tgtggatgcc tactagaact gggttagagc tacagctttc ttatacactt cgtcatcaac  1380
atcccgtgga gtatacggtt cctattcaat taccggtgat taaccaagtg tttggtacta  1440
gtagggctgt aaaaatatct cctaattctc ctgtggctag gttgagacct gtttctggga  1500
aatatatgct aggggaggtg gtcgctgtga gggttccgct tctccacctt tctaattttc  1560
agattaatga ctggcctgag cttctcaacaa agagatatgc tttgatggtt ttgatgcttc  1620
cttcagatag tgcaaggcaa tggcatgtcc atgagttgga actcgttgaa gtcgtcgctg  1680
atcaggtttt acattgctga gaatttctct tctttgctat gttcatgatc ttgtctataa  1740
```

-continued

```
cttttcttct cttattatag gtggctgtag ctctctcaca tgctgcgatc ctagaagagt    1800
cgatgcgagc tagggacctt ctcatggagc agaatgttgc tcttgatcta gctagacgag    1860
aagcagaaac agcaatccgt gcccgcaatg atttcctagc ggttatgaac catgaaatgc    1920
gaacaccgat gcatgcgatt attgcactct cttccttact ccaagaaacg gaactaaccc    1980
ctgaacaaag actgatggtg gaaacaatac ttaaaagtag taaccttttg gcaactttga    2040
tgaatgatgt cttagatctt tcaaggttag aagatggaag tcttcaactt gaacttggga    2100
cattcaatct tcatacatta tttagagagg taacttttga acagctctat gtttcataag    2160
tttatactat ttgtgtactt gattgtcata ttgaatcttg ttgcaggtcc tcaatctgat    2220
aaagcctata gcggttgtta agaaattacc catcacacta aatcttgcac cagatttgcc    2280
agaatttgtt gttggggatg agaaacggc aatgcagata atattaaata tagttggtaa    2340
tgctgtgaaa ttctccaaac aaggtagtat ctccgtaacc gctcttgtca ccaagtcaga    2400
cacacgagct gctgactttt tgtcgtgcc aactgggagt catttctact tgagagtgaa    2460
ggttattatc ttgtatcttg ggatcttata ccatagctga aagtatttct taggtcttaa    2520
ttttgatgat tattcaaata taggtaaaag actctggagc aggaataaat cctcaagaca    2580
ttccaaagat tttcactaaa tttgctcaaa cacaatcttt agcgacgaga agctcgggtg    2640
gtagtgggct tggcctcgcc atctccaaga ggtttgagcc ttattaaaag acgttttttt    2700
ccaactttt cttgtcttct gtgttgttaa agtttactc ataagcgttt aatatgacaa    2760
ggtttgtgaa tctgatggag ggtaacattt ggattgagag cgatggtctt ggaaaaggat    2820
gcacggctat ctttgatgtt aaacttggga tctcagaacg ttcaaacgaa tctaaacagt    2880
cgggcatacc gaaagttcca gccattcccc gacattcaaa tttcactgga cttaaggttc    2940
ttgtcatgga tgagaacggg ttagtataag cttctcacct ttctctttgc aaaatctctc    3000
gccttacttc ttgcaaatgc agatattggc gtttagaaaa aacgcaaatt taatcttatg    3060
agaaaccgat gattattttg gttgcagggt aagtagaatg gtgacgaagg gacttcttgt    3120
acaccttggg tgcgaagtga ccacggtgag ttcaaacgag gagtgtctcc gagttgtgtc    3180
ccatgagcac aaagtggtct tcatggacgt gtgcatgccc ggggtcgaaa actaccaaat    3240
cgctctccgt attcacgaga aattcacaaa acaacgccac caacggccac tacttgtggc    3300
actcagtggt aacactgaca aatccacaaa agagaaatgc atgagctttg gtctagacgg    3360
tgtgttgctc aaacccgtat cactagacaa cataagagat gttctgtctg atcttctcga    3420
gccccgggta ctgtacgagg gcatgtaaag gcgatggatg ccccatgccc cagaggagta    3480
attccgctcc cgccttcttc tcccgtaaaa catcggaagc tgatgttctc tggtttaatt    3540
gtgtacatat cagagattgt cggagcgttt tggatgatat cttaaaacag aaagggaata    3600
acaaaataga aactctaaac cggtatgtgt ccgtggcgat ttcggttata gaggaacaag    3660
atggtggtgg tataatcata ccatttcaga ttacatgttt gactaatgtt gtatccttat    3720
atatgtagtt acattcttat aagaatttgg atcgagttat ggatgcttgt tgcgtgcatg    3780
tatgacattg atgcagtatt atggcgtcag ctttgcgccg cttagtagaa caacaacaat    3840
ggcgttactt agtttctcaa tcaacccgat ctccaaaac                           3879
```

```
<210> SEQ ID NO 11
<211> LENGTH: 1200
<212> TYPE: DNA
<213> ORGANISM: Arabidopsis thaliana
<220> FEATURE:
<221> NAME/KEY: CDS
```

<222> LOCATION: (53)...(1024)

<400> SEQUENCE: 11

```
cgttgctgtc gaagttaggc caagaaaccc atttaaaaaa aaagagagag agatggagag      60
tttcccgatc atcaatctcg agaagcttaa tggagaagag agagcaatca ctatggagaa     120
gatcaaagac gcttgtgaaa actggggctt ctttgagtgt gtgaaccatg ggatttcact     180
cgagcttttg dacaaagtgg agaagatgac caaggaacat tacaagaagt gcatggaaga     240
gagattcaag gaatcgatta agaacagagg tcttgactct cttcgctctg aagtcaacga     300
cgttgactgg gaatccactt tctacctcaa gcaccttccc gtctctaata tctccgatgt     360
ccctgatctc gacgacgatt acagaacgtt aatgaaagac ttcgccggaa agatagagaa     420
gttgtcggag gagctactgg atctgctgtg cgagaatctc ggtttagaga agggttattt     480
aaaaaaggtg ttttacgggt cgaaaagacc gacttttgga accaaagtca gcaattatcc     540
accttgtcct aatccggacc tagtcaaggg tctccgagcc cacaccgacg ccggcggcat     600
catcctcctc ttccaagacg acaaagtcag tggacttcag cttcttaaag acggcgagtg     660
ggtcgatgtt cctccggtta agcattcaat cgtcgttaat ctcggcgatc aacttgaggt     720
gataaccaat gggaagtaca agagtgtgga acatagagtg ctatctcaga cagacggaga     780
aggaagaatg tcgatcgcat cattctataa tccgggaagc gactctgtta ttttttccggt     840
gccggagctg atcggaaaag aagcagagaa ggagaagaaa gagaactatc cgagatttgt     900
gtttgaagat tacatgaaac tctactctgc tgtcaagttt caggccaagg aaccaaggtt     960
tgaagccatg aaagctatgg agacaactgt ggccaacaat gttggaccat ggccactgc    1020
gtgaatgata tgtaactggt taataaatat atatatatat atatatatag tctttatata    1080
atgtcttaga aacttgatta ttcactatac gaataatttt gttcatgttg ttgtatgttt    1140
aagtggtgaa tgtgttatat atgggaatta atgttttctg ttcgaaaaaa aaaaaaaaaa    1200
```

<210> SEQ ID NO 12
<211> LENGTH: 3438
<212> TYPE: DNA
<213> ORGANISM: Arabidopsis thaliana
<220> FEATURE:
<221> NAME/KEY: exon
<222> LOCATION: (1212)...(1358)
<223> OTHER INFORMATION: Exon 1
<220> FEATURE:
<221> NAME/KEY: exon
<222> LOCATION: (1461)...(1592)
<223> OTHER INFORMATION: Exon 2
<220> FEATURE:
<221> NAME/KEY: exon
<222> LOCATION: (1660)...(1820)
<223> OTHER INFORMATION: Exon 3
<220> FEATURE:
<221> NAME/KEY: exon
<222> LOCATION: (1909)...(2893)
<223> OTHER INFORMATION: Exon 4

<400> SEQUENCE: 12

```
gttactttc aaatcttccc tcatattata tagccattga tatcatagag gatgtgagtt       60
ttaacttaat atttacccgt ttgaaactag ctatttactt aaatatgaat tataatctag     120
tttaactacc aaaacatca tatggggaca agaaaaagta ataaacgta tggaaaattt      180
tgtagatgtt ataatggat aattattcaa gtgataatct atcactttga tcttatctct     240
ttatccaatt taattacttt gtctctaagt gatttgcttc caaaatctaa gtgtagtcta    300
tcctatttct atcttatcct atcatataat cttctatata tatgtgagtc cgatgttgta   360
```

-continued

```
aagcgtacga gagagagtaa tgaagagtga agtgttatat tgttctctcg tccacttcca    420
ctctctcttt tatctcttac ttacttcttc gtaagatcat tacatataat aaataatatt    480
atttatgttt gtgttatatt taataacagt aaaaagtttt aaaacgttga aaaaattagc    540
cgacatagaa tacaaaagag ggttagcatc gggggagaaa cgtggaccaa catgatacac    600
cctccaaaat agtccccaag ttgaaacatt gacatgtttc gcttttctt ttctgtgtat     660 acttttttt tctgtgggtc acattattta atatttgtat acaagcagct attttacatg     720
gagatttcct gtcggtatag cgtcctcatt tctccatcgc ttccactttt ttcctatact    780
aatttgatct aattaattca tatgtcaaaa cattaagaaa atgaaactcg taattcatac    840
ttgaatttaa tagattaatt aaaatgctat ttattggcaa aataaactcg gtttatatct    900
aaattttaga atcactaaaa cttttgccc aaaaaaaat aaaataaat cactaaaaca       960 aaaaacaatc aaaagaaaac ccatgttggt aaatcggata tgaaaataa ttagaatccc    1020 cgtcctttgt gtattttggc gtagcatgaa actatataat aaacatgcat tcattcttag   1080
acttctcgta gcttatcaac aacaacgcgc tcgatctctc tcagcctgtc tgacaactct   1140
ttctctagtt ctagagttttt caatttattg ttgagccttt tattaaaaaa aaaaaaacaa   1200
gaacaaaaga aatggttcaa ttgtcaagaa aagctacatg caacagccat ggccaagtct   1260
cttcgtattt ccttggttgg gaagagtacg agaagaatcc ttacgacgtt accaagaacc   1320
ctcaaggcat tatccagatg ggtcttgcgg aaaatcaggt aaacaaatat tattcaacag   1380
catgtgatat atatatactt atgtatatca tgacagagag actaatttaa agtatgttta   1440 atttttattgg atttctgtag ctatgctttg atctactaga gtcatggctt gcacaaaaca   1500
cagacgcagc ctgtttcaag agagatggcc agtctgtttt ccgggaactc gctctctttc   1560
aagactacca tggcctctct tccttcaaaa atgtaagatt attaattgta tttatcaaat    1620
ttatttgtag gttgctgatc ttgctcgaat gattttcagg cctttgctga tttcatgtca   1680
gaaaatagag gaaatcgagt ttcttttgat tcaaacaacc ttgtgctcac tgctggagcc   1740
acttccgcaa acgagactct aatgttttgt cttgcagatc ccggtgacgc tttcttgctt   1800
cccacgccat attatccagg gttagtccac tgtttgctta cacgtaaaat ttccatcatt   1860
cctacgaact tgacttaact aaaactcatg tttattttg tacttcaggt ttgataggga   1920
tctaaaatgg cgaaccgggg ttgagattgt accaatccaa agctcaagta ctaacgggtt   1980 tcgcataacaa aaacttgcac tcgaagaagc ctacgagcaa gccaagaagc ttgacctaaa   2040
cgtcaaagga atactcatca ccaacccatc taaccctttg ggtacgacaa caacccaaac   2100
cgaactcaac attctatttg atttcatcac caagaataag aatatacatt tagtaagtga   2160
cgagatatat tcgggcacag tattcaactc ttcagaattc atcagcgtca tggagattct   2220
aaaaaataat caactcgaaa acaccgatgt tttgaaccga gtccacattg tttgtagctt   2280
atctaaagat ctaggcctcc ctggttttag agttggagcc atttactcca atgacaaaga   2340
tgtcatctct gccgctacaa aaatgtcaag tttcggcctt gtctcctccc agacacaata   2400
cctactatcc tcattattat ctgacaagaa gttcactaag aactacctta gagagaacca   2460
aaaacggctc aagaacagac agagaaagct cgtgttgggt ctagaggcca tcgggatcaa   2520
atgtctgaag agtaatgcgg gactcttttg ttgggtcgac atgagacctc tccttagatc   2580
taaaacgttc gaagcggaaa tggatctttg gaagaagatt gtttacgaag tgaagctcaa   2640
catctctcct ggttcgtcgt gccattgtga agaaccgggt tggtttagag tttgtttcgc   2700
```

```
gaacatgatt gatgagacat taaagcttgc tttaaagaga ttgaagatgt tggttgatga    2760
tgaaaactca agtagaagat gccaaaagag taaaagcgaa agactaaacg gttcgaggaa    2820
gaagacgatg tcaaatgtct ctaactgggt tttccgacta tcgtttcacg accgtgaggc    2880
tgaggaacga tagtccggtt tttgttttga agttcttttt ttttgtttcc cacacattgc    2940
aagtgattct gtaatttttt ttatcacgag agagagtgta aaaaaatgga aatgcaacgt    3000
gcttactctg atcctagatt ttagaaaacc gttgaagact tcttagagca agtccatcgg    3060
cagtttttaa tgggtttcta atgggtttct agctaattaa aagtccaaaa ttaaatgaaa    3120
acccaactaa ataattagga tccatcccaa tattaggttt tttggatggg ttttttagacg   3180 gcgacgtggt cgactgtgag tcgtcggaaa acaaaaaaaa tcacaacact catgttttcc    3240 ttttcctct cgttttcac ttttttgttt tgtccgacgg ccggcgattc gaatcgattt       3300
gatctccggt gtatcgaaca tgaaatcggg agagaagagc caaatcatcg acgacttggt    3360
tcaccaattc cattcttcga accatactca tataagagtt tcttggcttc tctctaaaac    3420
tcttctaatt ttctgata                                                   3438

<210> SEQ ID NO 13
<211> LENGTH: 68
<212> TYPE: DNA
<213> ORGANISM: Artificial Sequence
<220> FEATURE:
<223> OTHER INFORMATION: Beneficial Oligonucleotide-Contains both DNA
      and RNA

<400> SEQUENCE: 13
caggtcaagt gcaacgtagg atgattttta ucaaccuacg ttgcacuuga ccuggcgcgt    60
tttcgcgc                                                             68

<210> SEQ ID NO 14
<211> LENGTH: 68
<212> TYPE: DNA
<213> ORGANISM: Artificial Sequence
<220> FEATURE:
<223> OTHER INFORMATION: Beneficial Oligonucleotide-Contains Both DNA
      and RNA

<400> SEQUENCE: 14
caggtcaagt gctacgtagg atgattttta ucaaccuacg tagcacuuga ccuggcgcgt    60
tttcgcgc                                                             68

<210> SEQ ID NO 15
<211> LENGTH: 24
<212> TYPE: DNA
<213> ORGANISM: Jelly Fish

<400> SEQUENCE: 15
atggtgagca agggcgagga gctg                                           24

<210> SEQ ID NO 16
<211> LENGTH: 24
<212> TYPE: DNA
<213> ORGANISM: Artificial Sequence
<220> FEATURE:
<223> OTHER INFORMATION: Mutation

<400> SEQUENCE: 16
atggtgagca agggctagga gctg                                           24
```

-continued

```
<210> SEQ ID NO 17
<211> LENGTH: 24
<212> TYPE: DNA
<213> ORGANISM: Artificial Sequence
<220> FEATURE:
<223> OTHER INFORMATION: Mutation

<400> SEQUENCE: 17
atggtgagca agggcaggag ctgt                                          24

<210> SEQ ID NO 18
<211> LENGTH: 68
<212> TYPE: DNA
<213> ORGANISM: Artifical Sequence
<220> FEATURE:
<223> OTHER INFORMATION: Beneficial Oligonucleotide-Contains Both DNA
      and RNA

<400> SEQUENCE: 18
gtgagcaagg gcgaggagct gttcattttu gaacagcucc tcgcccuugc ucacgcgcgt    60
tttcgcgc                                                            68

<210> SEQ ID NO 19
<211> LENGTH: 68
<212> TYPE: DNA
<213> ORGANISM: Artificial Sequence
<220> FEATURE:
<223> OTHER INFORMATION: Beneficial Oligonucleotide-Contains Both DNA
      and RNA

<400> SEQUENCE: 19
tgagcaaggg ctcggagctg ttcacttttg ugaacagcuc cgagcccuug cucagcgcgt    60
tttcgcgc                                                            68
```